(12) United States Patent
Matsumura et al.

(10) Patent No.: US 7,993,837 B2
(45) Date of Patent: Aug. 9, 2011

(54) GENE EXPRESSION ANALYSIS USING ARRAY WITH IMMOBILIZED TAGS OF MORE THAN 25 BP (SUPERSAGE-ARRAY)

(75) Inventors: Hideo Matsumura, Iwate (JP); Ryohei Terauchi, Iwate (JP)

(73) Assignee: Iwate Prefectural Government, Morioka-Shi (JP)

( * ) Notice: Subject to any disclaimer, the term of this patent is extended or adjusted under 35 U.S.C. 154(b) by 125 days.

(21) Appl. No.: 12/213,183

(22) Filed: Jun. 16, 2008

(65) Prior Publication Data
US 2009/0082226 A1 Mar. 26, 2009

Related U.S. Application Data

(63) Continuation of application No. 11/635,688, filed on Dec. 8, 2006, now abandoned.

(30) Foreign Application Priority Data

Dec. 13, 2005 (JP) ................................. 2005-359366
May 18, 2006 (JP) ................................. 2006-138515

(51) Int. Cl.
*C12Q 1/68* (2006.01)
*C07H 21/02* (2006.01)
*C07H 21/04* (2006.01)

(52) U.S. Cl. ........................... 435/6; 536/23.1; 536/24.3
(58) Field of Classification Search ...... 435/6; 536/23.1, 536/24.3
See application file for complete search history.

(56) References Cited

U.S. PATENT DOCUMENTS

| | | | |
|---|---|---|---|
| 6,004,755 A | 12/1999 | Wang | |
| 6,040,138 A | 3/2000 | Lockhart et al. | |
| 2004/0023247 A1 | 2/2004 | Xu et al. | |
| 2008/0008993 A1 | 1/2008 | Kahl et al. | |

OTHER PUBLICATIONS

Matsumura et al. Gene expression analysis of plant host-pathogen interactions by SuperSAGE. PNAS 100(26) : 15718-15723 (2003).*
Velculescu et al., Serial Analysis of gene expression Science 270 484-487 (1995).
Yamamoto et al. Use of serial analysis of gene expression (SAGE) technology. J. of Immunological Methods 250 : 45-66 (2001).
Jongneel et al., Comprehensive sampling of gene expression in human cell lines with massively parallel signature sequencing. PNAS 100(8) : 4702-4705 (2003).
Brenner et al., In vitro cloning of complex mixtures of DNA on microbeads: Physical separation of differentially expressed cDNAs. PNAS 97(4) : 1665-1670 (2000).
Saha et al., Using the transcriptome to annotate the genome. Nature Biotechnology 19 : 509-512 (2002).
Pleasance et al. Assessment of SAGE in transcript identification. Genome Research 13 : 1203-1215 (2003).
Matsumura et al., Gene expression analysis of plant host-pathogen interactions by SuperSAGE. PNAS 100 (26) : 15,718-15,723 (Dec. 2003).
Matsumura et al. SuperSAGE array: the direct use of 26-base-pair transcript tags in oligonucleotide arrays. Nature Methods 3(6) : 469-474 (Jun. 2006).
Roberts et al., Rebase Enzyme Types, Nucl. Acids Res., vol. 31, pp. 1805-1812, 2005.

* cited by examiner

*Primary Examiner* — Ethan Whisenant
(74) *Attorney, Agent, or Firm* — Birch, Stewart, Kolasch & Birch, LLP

(57) ABSTRACT

This invention provides a method of gene expression analysis that enables extensive gene expression analysis and simultaneous analysis of multiple samples of organisms for which genomic analysis has not yet been advanced. In this method, tags each comprising an oligonucleotide of more than 25 bp for identifying expressed genes, wherein the 3'-end of the tag is defined by a cleavage site of a type III restriction enzyme and the 5'-end thereof is defined by a cleavage site of another restriction enzyme located closest to the 3'-end of the cDNA of such genes, are immobilized on a solid support, gene-containing samples are hybridized to the solid support, and the signals emitted from the genes hybridized to the tags are detected to analyze the gene expression profiles in the samples.

10 Claims, 8 Drawing Sheets
(5 of 8 Drawing Sheet(s) Filed in Color)

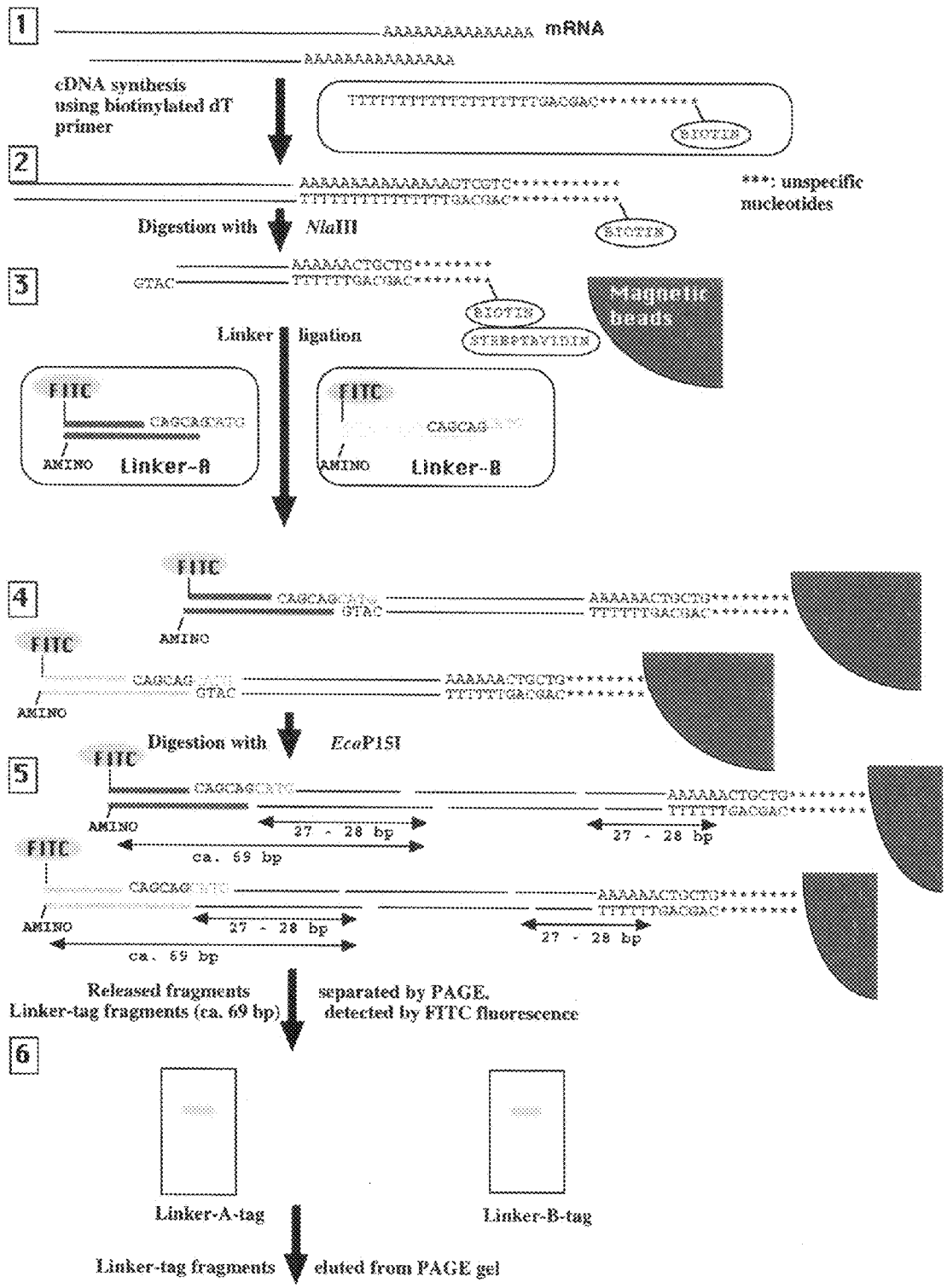

Fig. 5

| A | B | C | D |
|---|---|---|---|
| NbCD1U1 | NbCD1D1 | NbCD3U1 | NbCD3D1 |
| NbCD1U2 | NbCD1D2 | NbCD3U2 | NbCD3D2 |
| NbCD1U3 | NbCD1D3 | NbCD3U3 | NbCD3D3 |
| NbCD1U4 | NbCD1D4 | NbCD3U4 | NbCD3D4 |
| NbCD1U5 | NbCD1D5 | NbCD3U5 | NbCD3D5 |
| NbCD1U6 | NbCD1D6 | NbCD3U6 | NbCD3D6 |
| NbCD1U7 | NbCD1D7 | NbCD3U7 | NbCD3D7 |
| NbCD1U8 | NbCD1D8 | NbCD3U8 | NbCD3D8 |
| NbCD1U9 | NbCD1D9 | NbCD3U9 | NbCD3D9 |
| NbCD1U10 | NbCD1D10 | NbCD3U10 | NbCD3D10 |
| NbCD1U11 | NbCD1D11 | NbCD3U11 | NbCD3D11 |
| NbCD1U12 | NbCD1D12 | NbCD3U12 | NbCD3D12 |
| NbCD1U13 | NbCD1D13 | NbCD3U13 | NbCD3D13 |
| NbCD1U14 | NbCD1D14 | NbCD3U14 | NbCD3D14 |
| NbCD1U15 | NbCD1D15 | NbCD3U15 | NbCD3D15 |
| NbCD1U16 | NbCD1D16 | NbCD3U16 | NbCD3D16 |
| NbCD1U17 | NbCD1D17 | NbCD3U17 | NbCD3D17 |
| NbCD1U18 | NbCD1D18 | NbCD3U18 | NbCD3D18 |
| NbCD1U19 | NbCD1D19 | NbCD3U19 | NbCD3D19 |
| NbCD1U20 | NbCD1D20 | NbCD3U20 | NbCD3D20 |
| NbCD1U21 | NbCD1D21 | NbCD3U21 | NbCD3D21 |
| NbCD1U22 | NbCD1D22 | NbCD3U22 | NbCD3D22 |
| NbCD1U23 | NbCD1D23 | NbCD3U23 | NbCD3D23 |
| NbCD1U24 | NbCD1D24 | NbCD3U24 | NbCD3D24 |
| NbCD1U25 | NbCD1D25 | NbCD3U25 | NbCD3D25 |
| NbCD1U26 | NbCD1D26 | NbCD3U26 | NbCD3D26 |
| NbCD1U27 | NbCD1D27 | NbCD3U27 | NbCD3D27 |
| NbCD1U28 | NbCD1D28 | NbCD3U28 | NbCD3D28 |
| NbCD1U29 | NbCD1D29 | NbCD3U29 | NbCD3D29 |
| NbCD1U30 | NbCD1D30 | NbCD3U30 | |
| NbCD1U31 | NbCD1D31 | NbCD3U31 | |
| NbCD1U32 | NbCD1D32 | NbCD3U32 | |
| NbCD1U33 | NbCD1D33 | NbCD3U33 | |
| NbCD1U34 | NbCD1D34 | NbCD3U34 | |
| NbCD1U35 | NbCD1D35 | NbCD3U35 | |
| NbCD1U36 | NbCD1D36 | NbCD3U36 | |
| NbCD1U37 | NbCD1D37 | NbCD3U37 | |
| NbCD1U38 | NbCD1D38 | NbCD3U38 | |
| NbCD1U39 | NbCD1D39 | NbCD3U39 | |
| NbCD1U40 | | NbCD3U40 | |
| NbCD1U41 | | NbCD3U41 | |
| NbCD1U42 | | NbCD3U42 | |
| NbCD1U43 | | | |
| NbCD1U44 | | | |

GENE EXPRESSION ANALYSIS USING ARRAY WITH IMMOBILIZED TAGS OF MORE THAN 25 BP (SUPERSAGE-ARRAY)

CROSS-REFERENCE TO RELATED APPLICATIONS

This application is a Continuation of U.S. application Ser. No. 11/635,688, which was filed Dec. 8, 2006 now abandoned, which claims priority to Japanese applications JP2005-359366 filed on Dec. 13, 2005, and JP2006-138515 filed on May 18, 2006, the content of which is hereby incorporated by reference into this application.

TECHNICAL FIELD

The present invention relates to a method of gene expression analysis. More particularly, the present invention relates to a method of gene expression analysis that enables highly reproducible and high-throughput analysis, with the use of a microarray with immobilized improved SAGE™ tags of more than 25 bp.

BACKGROUND ART

Techniques for transcript analysis, such as microarray analysis and serial analysis of gene expression (SAGE™), are indispensable for various types of biological research. Use of a microarray enables the expression analysis of large quantities of genes at one time and simultaneous analysis of multiple samples. With the use of a microarray, however, expression analysis can only be conducted exclusively for the genes spotted on the array. Accordingly, it is necessary to prepare an array upon which all relevant genes may be spotted, in order to perform extensive analysis. In the case of model organisms, such as rice or *Arabidopsis thaliana*, cDNA arrays or oligonucleotide arrays covering all genes thereof are commercially available and are generally employed in research. Concerning many other organisms, however, researchers are required to independently design arrays from cDNA libraries. This requires large amounts of time and cost.

In contrast, serial analysis of gene expression (SAGE™) enables the search for novel genes and the quantitative expression analysis thereof (Velculescu et al., Science 270: 484-487, 1995). With this technique, the genes are identified based on a 10- or 11-bp sequence located downstream of the restriction enzyme site (CATG), which is located closest to the 3'-end of the transcript, and the expression levels of such genes are analyzed. Accordingly, sequential reading of the sequences located around the 3'-end with the use of a DNA sequencer enables the extensive expression analysis of genes, including unknown genes. However, SAGE™ is not substantially suitable for simultaneous analysis of multiple samples due to the large number of experimental steps required. In addition, 14-bp SAGE™ tags and 21-bp tags that are employed in LongSAGE™ (Saha et al., Nature Biotechnology 20, 508-512, 2002) are too short to assuredly identify genes. Thus, applications of such tags are restricted to model organisms.

In recent years, the present inventors had developed the SuperSAGE system, which is an improvement over SAGE™ (WO 2004/099445; Gene expression analysis of plant host-pathogen interactions by SuperSAGE, Matsumura, H., Reich, S., Ito, A., Saitoh, H., Kamoun, S., Winter, P., Kahl, G., Reuter, M., Krueger, D., and Terauchi R., 2003, Proc. Natl. Acad. Sci. U.S.A., 100: 15718-15723; Molekulares Wechselspiel von Wirt und Pathogen: Simultane, genomweite Transkriptprofilierung zweier Organismen mit SuperSAGE, Kahl, G., Winter, P., Matsumura, H., Reuter, M., Kruger, D. and Terauchi R., 2004, Biospektrum 10: 511-513; SuperSAGE, Matsumura, H., Ito, A., Saitoh, H., Winter, P., Kahl, G., Reuter, M., Krueger, D. H. and Terauchi, R., 2005, Cellular Microbiology, 2005, 7: 11-18; and SuperSAGE, a potent transcriptome tool for eukaryotic Organisms, Matsumura, H., Reich, S., Reuter, M., Krueger, D. H., Winter, P., Kahl, G. and Terauchi R., In: S.-M. WANG (ed.) SAGE: Current Technologies and Applications, Horizon Scientific Press, 2004, 77-90). SuperSAGE involves the use of a type III restriction enzyme, EcoP15I, to obtain a 26-bp nucleotide sequence tag. Use of tags each of 26 bp remarkably improves the accuracy of gene identification. Such tags also enable simultaneous analysis of gene expression both in host cells and in pathogen cells, and applications thereof became available with regard to non-model organisms, for which no DNA database is available.

DISCLOSURE OF THE INVENTION

It is an object of the present invention to provide a method of gene expression analysis that enables extensive gene expression analysis and simultaneous analysis of multiple samples of organisms for which the genomic analysis has not yet been advanced.

In order to attain the above object, the present inventors had examined whether or not tags each of 26 bp of SuperSAGE (SuperSAGE tags) could be utilized as probes for microarrays. As a result, they discovered that the results of gene expression analysis attained with the use of an array with immobilized SuperSAGE tags would be similar to those attained via conventional SAGE™, and that such results could be attained through a single hybridization step. Further, they also discovered that immobilization of SuperSAGE tags would produce unexpected effects, i.e., preparation of microarrays would be remarkably facilitated in non-model organisms for which no EST, cDNA, or genomic sequences are available.

More specifically, the present invention relates to a solid support onto which tags each comprising an oligonucleotide of more than 25 bp for identifying the expressed genes are immobilized, wherein the 3'-end of the tag is defined by a cleavage site of a type III restriction enzyme and the 5'-end thereof is defined by a cleavage site of the other restriction enzyme located closest to the 3'-end of the cDNA of such genes. The present invention also relates to a method of gene expression analysis involving the use of such solid support with immobilized tags.

The sequences of the tags according to the present invention (i.e., SuperSAGE tags) can be determined based on the SuperSAGE system that the present inventors previously developed (WO 2004/099445). Specifically, such tag sequences are determined in accordance with the following steps:

1) a cDNA pool is synthesized from mRNAs of expressed genes using a primer comprising a recognition sequence of a type III restriction enzyme and an oligo-dT sequence, and treating the cDNA pool with another restriction enzyme;

2) a poly(A)-containing fragment is purified from the cDNA pool, and such fragment is ligated to a linker A or B;

3) the fragment is treated with a type III restriction enzyme, and the resulting linker A-containing fragment is ligated to a linker B-containing fragment;

4) linker sequences are removed by cleaving the ligated fragments with another restriction enzyme used in step 1) to obtain ditag oligonucleotides;

5) ditag oligonucleotides are ligated to each other to prepare polynucleotides; and 6) the nucleotide sequences of the above polynucleotides are analyzed to determine the nucleotide sequences of tags contained in such polynucleotides.

Examples of type III restriction enzymes that can be used in the present invention are disclosed at a web site (http://rebase.neb.com/cgi-bin/azlist?re3), and examples thereof include EcoPI and EcoP15I.

Examples of other restriction enzymes (commercial products) include those shown in the table below.

| Recognition sequence | Enzymes (commercial products only) |
|---|---|
| CATG^ | NlaIII, Hsp92II, |
| ^CATG | FatI |
| C^TAG | BfaI, MaeI, XspI |
| A^CGT | HpyCH4IV, MaeII, |
| ACGT^ | TaiI, TscI |
| AG^CT | AluI |
| T^CGA | TaqI |
| ^GATC | BfuCI, Bsp143I, BstENII, DpnII, Kzo9I, MboI, NdeII, Sau3AI |
| GAT^C | BstKTI, |
| G^TAC | Csp6I |

As a preferred embodiment of the present invention, use of EcoP15I and NlaIII is described in the Examples below. When EcoP15I and NlaIII are used, the aforementioned linker A and linker B are double-stranded DNAs that are different from each other and that are obtained by annealing the following first strand of DNA (1) and the second strand of DNA (2):

DNA (1): 5'-N$_{30-40}$-CAGCAGCATG-3'     (SEQ ID NO: 201)

DNA (2): 3'-N$_{30-40}$-GTCGTC-5' wherein "N$_{30-40}$" of DNA (1) is complementary to "N$_{30-40}$" of DNA (2), each thereof is a sequence comprising 30 to 40 arbitrary nucleotides, the 5'-end of DNA (1) may be labeled, and the 3'-end of DNA (2) may be amino-modified.

The array according to the present invention may be prepared by synthesizing tag oligonucleotides on the solid support. Alternatively, the array may be prepared by immobilizing pre-synthesized tag oligonucleotides on the solid support.

The present invention facilitates the extensive gene expression analysis and simultaneous analysis of multiple samples of organisms for which genomic analysis has not yet been advanced. Accordingly, the present invention overcomes the drawbacks of conventional microarray or SAGE™ systems and realizes extensive analysis of known and unknown genes.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 1-1 schematically shows a method for preparing SuperSAGE tags (SEQ ID NOs: 202-210).

FIG. 1-2 schematically shows a method for preparing SuperSAGE tags (SEQ ID NO: 211).

FIG. 2 schematically shows the SuperSAGE-Array according to the present invention. SuperSAGE detects a 26-bp tag sequence of a gene with an expression level that varies among 2 or more samples. Microarrays are prepared with oligonucleotides of these tag sequences (SuperSAGE-Array) (SEQ ID NOs: 52-55 and 89-92). These arrays enable high-throughput analysis of multiple samples.

FIG. 5 shows the gene expression profiles in NbCD1- or NbCD3-overexpressing Nicotiana benthamiana leaves analyzed via SuperSAGE-Array. Based on the results of SuperSAGE-Array analysis, genes were classified as follows: (A) genes induced upon NbCD1 overexpression; (B) genes repressed upon NbCD1 overexpression; (C) genes induced upon NbCD3 overexpression; and (D) genes repressed upon NbCD3 overexpression. Compared with the control GFP-overexpressing leaves, stronger signals are represented by red tiles and weaker signals are represented by green tiles.

PREFERRED EMBODIMENTS OF THE INVENTION

Figures 1, 2:
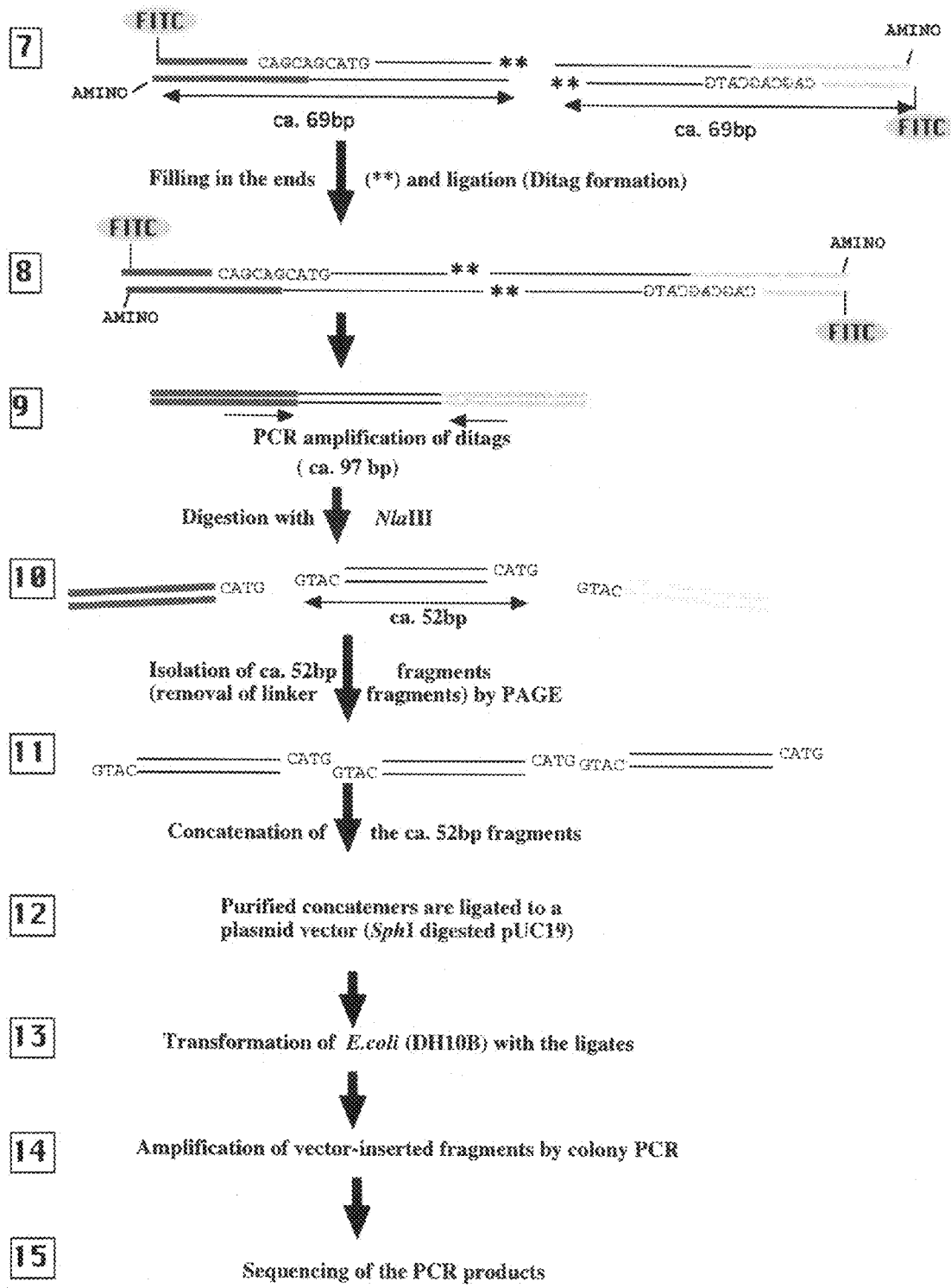
Figure 2:
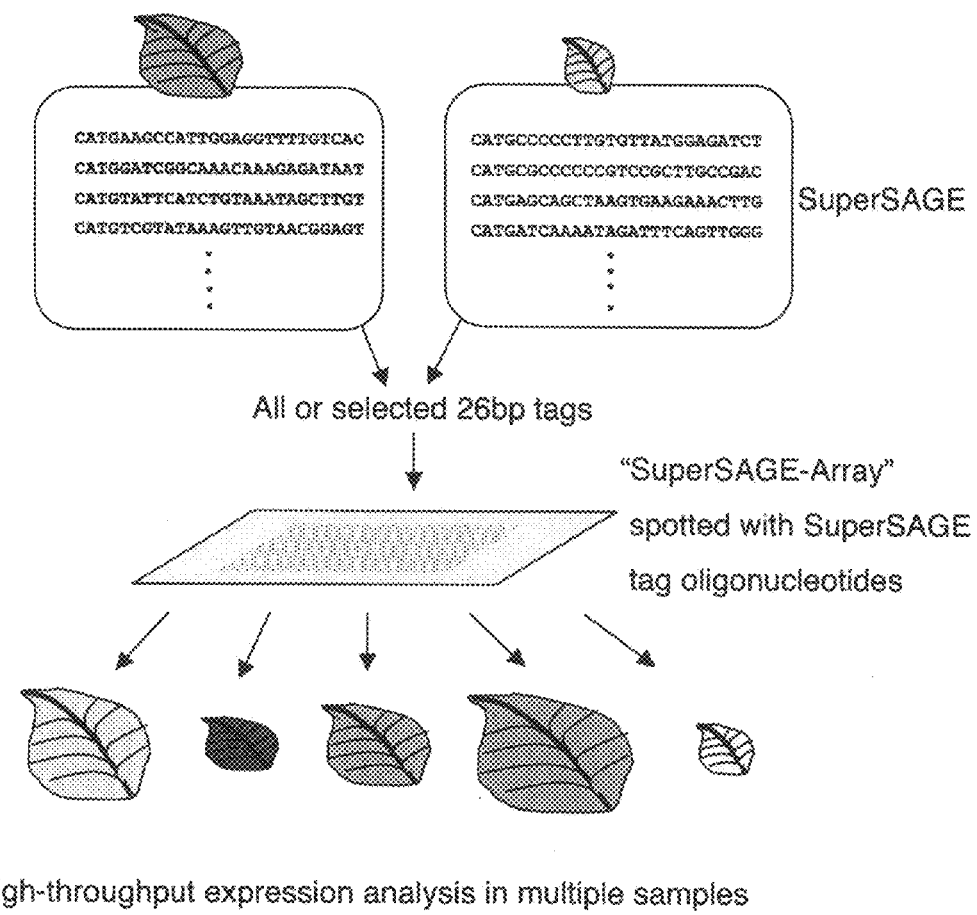

The present invention relates to a method for expression analysis of genes of various organisms with the use of a solid support with immobilized tags of more than 25 bp obtained via SuperSAGE. The solid support (array) with immobilized tags used in the present invention is prepared by SuperSAGE in combination with microarray techniques. This array is referred to as a "SuperSAGE-Array" herein (FIG. 2). A method for preparing a SuperSAGE-Array and a method of gene expression analysis using the same are hereafter described in detail.

1. Preparation of SuperSAGE Tag

A method for determining a tag sequence of more than 25 bp (a SuperSAGE tag) for identifying a gene of a target organism via the SuperSAGE method developed by the present inventors is first described with reference to FIG. 1. Details of SuperSAGE as employed herein are described in the following publications: Matsumura, H., et al., 2003, Proc. Natl. Acad. Sci. U.S.A., 100: 15718-15723; Kahl, G. et al., 2004, Biospektrum 10: 511-513; Matsumra, H. et al., 2005, Cellular Microbiology, 2005, 7: 11-18; Matsumura, H. et al., Current Technologies and Applications, Horizon Scientific Press, 2004, 77-90; and WO 2004/099445.

In accordance with a conventional technique, total RNA or mRNA is prepared from a specimen of a target organism, and cDNA is synthesized with the use of such total RNA or mRNA as a template and a biotinylated oligo-dT primer (a reverse transcription primer). This reverse transcription primer comprises 18 to 25 nucleotides, the 5'-CAGCAG-3' sequence, which is a recognition sequence of the EcoP15I enzyme, and 15- to 25-mer dT subsequent thereto (Step 1, FIG. 1). The type III restriction and modifying enzyme, EcoP15I, recognizes CAGCAG sequences from among the target DNA molecules and cleaves the recognized sequence at a site 25 to 28 nucleotides away from the 3'-end thereof.

The synthesized cDNA is digested with a CATG-recognizing restriction enzyme, NlaIII, and a digestion fragment containing the biotinylated reverse transcription primer sequence is solely recovered by streptavidin-coated magnetic beads (Steps 2 and 3, FIG. 1).

Subsequently, two types of linkers, i.e., linker A and linker B (each comprising 46 nucleotides), are ligated to the ends of a cDNA fragment captured by magnetic beads. The linker comprises a CAGCAG sequence, which is a recognition sequence of the EcoP15I enzyme (Step 4, FIG. 1).

The obtained cDNA pool is divided into two sections, and one of them is ligated to linker A and the other is ligated to linker B. The resultants are designated as "linker A-ligated cDNA" and "linker B-ligated cDNA," respectively.

DNA fragments of both "linker A-ligated cDNA" and "linker B-ligated cDNA" that had been bound to magnetic beads are each digested with EcoP15I and magnetic beads are then removed (Step 5, FIG. 1). After the digestion, one of the fragments comprises a linker and the 27- or 28-bp tag sequence (with a total size of 69 or 70 bp), and the other fragment is of a variable size contained in a double-stranded cDNA fragment. A poly(A)-containing fragment remains bound to magnetic beads, and this fragment is not involved in subsequent procedures.

A 69- or 70-bp fragment comprising a linker sequence and the 27- or 28-bp tag sequence is visualized with FITC under UV irradiation, and such fragment is isolated from polyacrylamide gel via gel excision.

Fragments of 69 or 70 bp obtained from linker A-ligated cDNA and linker B-ligated cDNA (i.e., tag-linker fragments) are blunted via a 3'-filling reaction, and these fragments are ligated to each other to form "ditags." The 3'-end of the linker fragment is blocked via amino-modification. Thus, such ligation takes place only at a site between cDNA tag sequences (Steps 6 and 7, FIG. 1).

The resulting "ditag" molecules are amplified by PCR (Step 8, FIG. 1). PCR primers are constructed from linker sequences and the PCR products are of ca. 97 bp.

The PCR products of ca. 97 bp are digested with NlaIII (Step 10, FIG. 1) to result in "ditag" fragments of ca. 52 bp. These fragments are isolated from gel and then purified.

The "ditag" fragments are further ligated (Step 11, FIG. 1) to result in concatemers. The concatemers are subjected to agarose gel electrophoresis, and fragments of 500 or more bp are isolated from gel.

The size-separated concatemer fragments are cloned into adequate plasmid vectors that have been treated with SphI and CIP (Step 12, FIG. 1). The resulting plasmids are then transformed into *E. coli* (Step 13, FIG. 1).

Subsequently, fragments that were inserted into plasmids are amplified by PCR (Step 14, FIG. 1).

A nucleotide sequence is directly read from the PCR product (Step 15, FIG. 1).

A ditag of ca. 44 bp is present and is flanked by the recognition sequences of NlaIII, i.e., CATG. Information concerning a ca. 52-bp (44+8) sequence indicates two 26-bp to 28-bp tag sequences isolated from specific regions in each cDNA.

Via sequencing of several clones of nucleotide sequences, SuperSAGE tag sequences derived from various organisms shown in Tables 1 to 5 are obtained.

2. Tag Immobilization—Preparation of SuperSAGE-Array

Based on the sequence information concerning the resulting SuperSAGE tag oligonucleotides are synthesized and immobilized on an adequate solid support to prepare the array according to the present invention (e.g., SuperSAGE-Array). The array according to the present invention is not limited to a microarray, and examples thereof include a bead array, a membrane filter, and a capillaries. In the step of synthesizing such tags, desired functional groups may be introduced onto the ends of the tags with the use of primers labeled at their 5'-ends with functional groups such as thiol groups, in order to enhance the efficiency of immobilizing tags upon the substrate.

Tags may be immobilized upon a substrate by any means without particular limitation. Oligonucleotides may be directly synthesized on a substrate made of glass, metal, silicon, or the like (Affymetrix type). Pre-synthesized oligonucleotides may be spotted to a substrate (standard type). Alternatively, tags may be immobilized in a filter made of nylon, nitrocellulose, or the like. A glass substrate or the like has a small effective area for immobilization and a low charge. Thus, the surface of such substrate is preferably treated with polysilane, silane, polycarbodiimide, aminosilane, or the like, in order to enhance the efficiency of tag immobilization. Use of commercially available substrates, such as polylysine- or silane-coated glass substrates, the surfaces of which are treated with the aforementioned substances, is also preferable.

In general, pre-synthesized tags are automatically immobilized on a substrate using a spotter. In order to compare tag information and signals transmitted from tags, it is preferable that the sites of gene immobilization be fully known. Sites of tag immobilization are not particularly limited, provided that such comparison can be made.

3. Gene Expression Analysis Using SuperSAGE-Array

In accordance with a conventional technique, total RNA is extracted from a sample to prepare mRNA or cDNA. The target is labeled with an adequate fluorescent reagent (e.g., Cy3-UDP or Cy5-UDP) in advance, when mRNA or cDNA is prepared from the sample. The labeled target is hybridized to the aforementioned substrate with an immobilized tag and then washed. Thereafter, fluorescence intensities (signal intensities) at the sites of tag immobilization are assayed. The fluorescence intensities read with a scanner may be subjected to error adjustment or normalization of variations among samples, according to need. Normalization can be carried out based on the genes that are commonly expressed in samples, such as housekeeping genes. Further, a reliability limit may be determined to eliminate the data exhibiting low correlation.

4. Application of SuperSAGE-Array

Gene expression analysis that is carried out using the solid support according to the present invention (SuperSAGE-Array) can be a useful and fundamental technique for extensive gene expression analysis for any eukaryotic organism. Many of currently available microarray techniques depend on EST, cDNA, or genomic sequences. Non-redundant cDNA sequences are required for the preparation of arrays. To this end, it is necessary to prepare a cDNA library that is normalized or that represents the genes differentially expressed between the two samples. The solid support with immobilized tags (SuperSAGE-Array) according to the present invention becomes a crucial technique for preparing such arrays.

According to the present invention, information concerning a large number of expressed genes can be attained within a shorter period of time than is possible with large-scale EST analysis. The SuperSAGE tags that are employed in the present invention are obtained from specific sites in the exons. Thus, each tag is unique to each gene. With the utilization of such characteristics, oligoarrays of expressed genes can be easily prepared for any tissues or under any conditions.

For example, the SuperSAGE-Array obtained from a variety of cancer tissues is useful for clinical testing, and Super-SAGE-Arrays can be used for all eukaryotic organisms. If the tags exhibiting the expression patterns of interest were found, a partial cDNA fragment can be obtained by the 3'-RACE method using a tag sequence of 26 bp. The RACE product may be subjected to BLAST search to identify the genes represented by such tags.

Microarrays of host organism and pathogen genes can be applied to the host-pathogen interaction analysis. The present inventors can easily prepare such arrays via the SuperSAGE-Array system. By using SuperSAGE for pathogen-infected tissues, an array with host and pathogen genes spotted thereon can be easily prepared. Use of such array enables high-throughput analysis of expression changes of genes derived from both host and pathogen, for example.

EXAMPLES

The present invention is hereafter described in greater detail with reference to the examples, although the present invention is not limited to these examples.

Example 1

1. Material and Method

1) Preparation of RNA

For rice SuperSAGE and oligoarray systems, rice leaves (variety: Yashiromochi) and suspension-cultured cells (variety: Kakehashi) were prepared. For the oligoarray system, mRNA was extracted from the rice (variety: Yashiromochi) and the cultured cells (variety: Kakehashi) 1 month after sowing using an mRNA Purification Kit (Amersham Pharmacia).

For *Nicotiana benthamiana* SuperSAGE and oligoarray systems, leaves into which *Agrobacterium* containing the following plasmids had been injected were prepared. Two days after the *Agrobacterium* injection, *Nicotiana benthamiana* leaves were treated with dexamethasone (DEX), and mRNA was extracted using the mRNA Purification Kit (Amersham Pharmacia) 4 hours later.

2) Plasmids

NbCD1 (JP Patent Publication (Unexamined) No. 2005-278634) and NbCD3 cDNA (JP Patent Publication (Unexamined) No. 2005-245251), which had been isolated by the present inventors in the past, were used. A binary plasmid having these cDNAs and GFP cDNA downstream of a GVG promoter (Aoyama T. and Chua N.-H., 1997, The Plant Journal, 1997, 11: 605-612) capable of specific induction of gene expression via glucocorticoid (dexamethasone) treatment was prepared.

3) SuperSAGE mRNAs extracted from rice and *Nicotiana benthamiana* were purified to obtain 3 to 5 µg of poly(A) RNA. A Super-SAGE library was prepared from this poly(A) RNA and data analysis was carried out in accordance the publications (cited above).

Specifically, the obtained poly(A) RNA was employed as a template and the oligo-dT primer (reverse transcription primer:

(SEQ ID NO: 8)
CTGATCTAGAGGTACCGGATCC<u>CAGCAG</u>TTTTTTTTTTTTTTTTTTT that had been biotinylated by the "cDNA Synthesis System" (Invitrogen) was used to synthesize cDNA. This reverse transcription primer comprises a 22 bp sequence, the 5'-CAG-CAG-3' sequence, which is a recognition sequence of the EcoP15I enzyme, and 19-mer dT subsequent thereto.

The synthesized cDNA was digested with the NlaIII restriction enzyme, and the digestion fragment containing the biotinylated reverse transcription primer sequence was selectively recovered with the use of streptavidin-coated magnetic beads.

Subsequently, the following two types of linkers, i.e., linker A and linker B (each comprising 46 nucleotides), were bound to the ends of a cDNA fragment captured by magnetic beads. These linkers comprised a CAGCAG sequence, which is a recognition sequence of the EcoP15I enzyme.

Linker A is a double-stranded sequence obtained by annealing the following two oligonucleotides.

(SEQ ID NO: 197)
FITC-5'-TTTGGATTTGCTGGTGCAGTACAACTAGGCTTAATA<u>CAGCAG</u>
CATG-3'

(SEQ ID NO: 198)
5'-<u>CTGCTG</u>TATTAAGCCTAGTTGTACTGCACCAGCAAATCCAAA-3'-
NH<sub>2</sub>.)

Linker B is a double-stranded sequence obtained by annealing the following two oligonucleotides.

(SEQ ID NO: 199)
FITC-5'-TTTCTGCTCGAATTCAAGCTTCTAACGATGTACG<u>CAGCAG</u>CA
TG-3'

(SEQ ID NO: 200)
5'-<u>CTGCTG</u>CGTACATCGTTAGAAGCTTGAATTCGAGCAGAAA-3'-
NH<sub>2</sub>.

The obtained cDNA pool was divided into two sections, one of them was ligated to linker A and the other was ligated to linker B. The resultants were designated as "linker A-ligated cDNA" and "linker B-ligated cDNA," respectively. They were digested with EcoP15I, magnetic beads were removed, and a fragment comprising a linker and the 27- or 28-bp tag sequence (with a total size of 69 or 70 bp) and a fragment of a variable size contained in a double-stranded cDNA fragment were obtained. A poly(A)-containing fragment remained bound to magnetic beads, and this fragment was not involved in subsequent procedures.

A 69- or 70-bp fragment comprising a linker sequence and the 27- or 28-bp tag sequence was visualized with FITC under UV irradiation, and such fragment was isolated from polyacrylamide gel via gel excision.

Fragments of 69- or 70-bp obtained from linker A-ligated cDNA and linker B-ligated cDNA (i.e., tag-linker fragments)

were blunted via a 3'-filling reaction, and these fragments were ligated to each other to form "ditags."

The resulting "ditag" molecules were amplified by PCR using primers containing linker sequences to obtain PCR products each of 97 bp. The PCR products of ca. 97 bp were digested with NlaIII to result in "ditag" fragments of ca. 52 bp. These fragments were isolated from gel and then purified.

The "ditag" fragments were further ligated to result in polynucleotides (concatemers). The concatemers were subjected to agarose gel electrophoresis, and fragments of 500 or more bp were isolated from gel.

The size-separated concatemer fragments were cloned into adequate plasmid vectors that have been treated with SphI and CIP. The resulting plasmids were then transformed into *E. coli*.

Subsequently, fragments that were inserted into plasmids were amplified by PCR, and the nucleotide sequences of the PCR products were analyzed with a sequencer. The PCR products each comprised a ditag of ca. 52 bp flanked by the recognition sequences of NlaIII, i.e., CATG. Information concerning a ca. 52 bp sequence indicated two 26-bp tag sequences isolated from specific regions in each cDNA.

Via sequencing of several clones of nucleotide sequences, SuperSAGE tag sequences derived from various organisms shown in Tables 1 to 5 were obtained.

4) Oligonucleotide Array Analysis

A SuperSAGE-Array was prepared using the 12-well NimbleGen array system. The design of the SuperSAGE-Array is described below in detail. Total RNA (20 μg each) was prepared from tissues, double-strand cDNAs were synthesized, and biotinylated cDNA probes were prepared via in vitro transcription. These biotinylated probes were labeled with Cy3 fluorescent dye. The labeled probes were hybridized, signals were read with a scanner, and the data of the signal values were standardized by the Robust Multi-chip Analysis (RMA) method. Array preparation and hybridization were entrusted to Gene Frontier.

2. SuperSAGE-Array of Model Rice Species

In order to actually test the performance of the Super-SAGE-Array, the transcript profiles in rice leaves and in cultured cells were first analyzed by the SuperSAGE method (WO 2004/099445). The tag sequences each of 26 bp (10,968 tags in the case of leaves and 10,044 tags in the case of cultured cells) were compared between two samples, and oligonucleotide arrays were prepared by selecting 7 tags expressed at substantially the same level in the two samples, 20 tags expressed at high levels only in leaves, and 14 tags expressed at high levels only in cultured cells (Table 1).

TABLE 1

SuperSAGE tags from rice spotted onto the SuperSAGE-Array

| | | Number of tags | | |
|---|---|---|---|---|
| Code | Tag sequence (5'->3') | Leaf | Suspension-cultured-cell | SEQ ID NO. |
| RSpCon1 | CATGAATTGAGTTCGCTTTGGTTATG | 78 | 98 | SEQ ID NO: 1 |
| RSpCon2 | CATGGTTTGGTTGGATTAGGCGGAGT | 40 | 26 | SEQ ID NO: 2 |
| RSpCon3 | CATGGGCTAAAGCCAGCCAAACTGGT | 12 | 21 | SEQ ID NO: 3 |
| RSpCon4 | CATGTCGGTTCAGTTATGTGAACTTG | 10 | 24 | SEQ ID NO: 4 |
| RSpCon5 | CATGTAATGTTTGCTATCGTGAGTTA | 10 | 11 | SEQ ID NO: 5 |
| RSpCon6 | CATGGCTGACCCAGCCTTCCGTCCAC | 10 | 10 | SEQ ID NO: 6 |
| RSpCon7 | CATGGGAGCGACTCCGTGGACAACGG | 12 | 19 | SEQ ID NO: 7 |
| RSpL1 | GATGTTCGGCTGCACCGATGCCACCC | 36 | 0 | SEQ ID NO: 9 |
| RSpL2 | CATGGGGACGCATCGCCTTCAGCTAA | 35 | 0 | SEQ ID NO: 10 |
| RSpL3 | CATGTAATATGATGCCTAGAGCATAT | 30 | 0 | SEQ ID NO: 11 |
| RSpL4 | CATGTAATGGTACATATCTCCTTGTT | 29 | 0 | SEQ ID NO: 12 |
| RSpL5 | CATGCTCAAGATGATCGAGGACTACC | 26 | 0 | SEQ ID NO: 13 |
| RSpL6 | CATGTATGTATGTCCCTTAATTGTGT | 26 | 0 | SEQ ID NO: 14 |
| RSpL7 | CATGTTGATATTGTATCAGCAAGCAC | 26 | 1 | SEQ ID NO: 15 |
| RSpL8 | CATGGACGAGCGCGACGCCAAGATCC | 25 | 0 | SEQ ID NO: 16 |
| RSpL9 | CATGGCGCAGGAGGTGCTTCTCGGCG | 24 | 0 | SEQ ID NO: 17 |
| RSpL10 | CATGTACTACTACCTTGTAAACTTTT | 24 | 0 | SEQ ID NO: 18 |
| RSpL11 | CATGTTCGGGTGCACTGACGCCACCC | 24 | 0 | SEQ ID NO: 19 |
| RSpL12 | CATGGGGGATTGTGCACGCATCTGGC | 21 | 0 | SEQ ID NO: 20 |
| RSpL13 | CATGTGTGTACGTGGTGTGTTTTGAG | 20 | 0 | SEQ ID NO: 21 |
| RSpL14 | CATGCATAATTGAACGCTTGTCGTGC | 18 | 0 | SEQ ID NO: 22 |

TABLE 1-continued

SuperSAGE tags from rice spotted onto the SuperSAGE-Array

| Code | Tag sequence (5'->3') | Number of tags Leaf | Suspension-cultured-cell | SEQ ID NO. |
|---|---|---|---|---|
| RSpL15 | CATGTGTAAATACTGCCGTGTGTTTC | 18 | 0 | SEQ ID NO: 23 |
| RSpL16 | CATGGATCCGTCTCTCTGGGAGGAAT | 120 | 0 | SEQ ID NO: 24 |
| RSpL17 | CATGTCGGACAAGTGCGGCAACTGCG | 111 | 0 | SEQ ID NO: 25 |
| RSpL18 | CATGTGGTGGCTTAGCTCTACGTGTA | 96 | 0 | SEQ ID NO: 26 |
| RSpL19 | CATGTTGTAATACTCCATCAAAGAGT | 81 | 0 | SEQ ID NO: 27 |
| RSpL20 | CATGCATATGTGAATGCTAGCACCAG | 48 | 0 | SEQ ID NO: 28 |
| RSpSus1 | CATGTGCTGTTGTGGCGTGTCGCTAG | 0 | 60 | SEQ ID NO: 29 |
| RSpSus2 | CATGCTTCAATATATATCCATCAAAT | 0 | 48 | SEQ ID NO: 30 |
| RSpSus3 | CATGGATTTGCACTGTCTGATCTATC | 1 | 46 | SEQ ID NO: 31 |
| RSpSus4 | CATGCACAACAGCACAAGTGGAGTAG | 0 | 40 | SEQ ID NO: 32 |
| RSpSus5 | CATGGTAATGTACCAAACAGCGATGA | 1 | 36 | SEQ ID NO: 33 |
| RSpSus6 | CATGCGTTTGTGGGCAAGAAGACAAT | 3 | 28 | SEQ ID NO: 34 |
| RSpSus7 | CATGCTGGTAGCTCAGCGAATCTCCT | 1 | 20 | SEQ ID NO: 35 |
| RSpSus8 | CATGGCACGGTTACCCGTCATTTCCG | 1 | 21 | SEQ ID NO: 36 |
| RSpSus9 | CATGATGATGGCCGCCACCGCCACCG | 0 | 18 | SEQ ID NO: 37 |
| RSpSus10 | CATGCGAGTTCCCGGGGCTCAAGATC | 0 | 19 | SEQ ID NO: 38 |
| RSpSus11 | CATGGCCACCGCTACCAACGGCAACG | 0 | 26 | SEQ ID NO: 39 |
| RSpSus12 | CATGGTCGCCGCCGCCGTGCCGGAGC | 0 | 32 | SEQ ID NO: 40 |
| RSpSus13 | CATGTGTGTTGTGTGTACGATGAGCT | 0 | 20 | SEQ ID NO: 41 |
| RSpSus14 | CATGTTAAGTTTGAGATATGATATGA | 0 | 15 | SEQ ID NO: 42 |

As described above, the SuperSAGE-Array was prepared using the 12-well array system (NimbleGen Inc. Co.) with direct synthesis of a 26-bp oligonucleotide on a glass substrate. Concerning the tag sequences, oligonucleotides carrying two-base mismatches in positions 7 and 13 of 26-bp SuperSAGE tag sequences were also synthesized and used for a hybridization specificity test.

Figure 3:
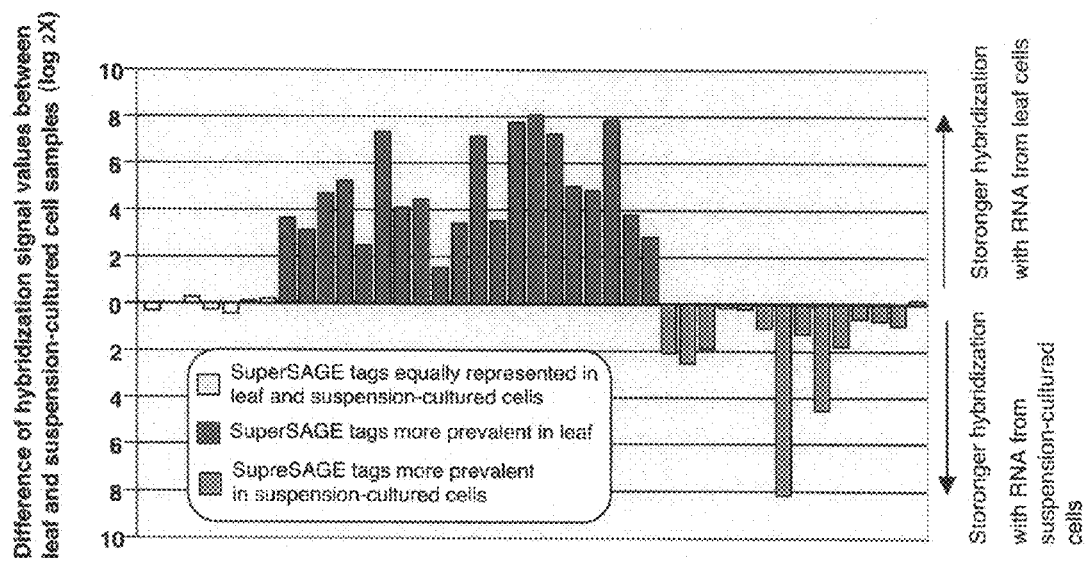
FIG. 3 shows the results of gene expression analysis via SuperSAGE-Array analysis in rice leaves and in cultured cells. The heights of the bar charts represent the differences of the standardized signal values between rice leaves and cultured cells (represented in terms of log values). The more the bar chart extends upward from level 0, the stronger the signals in leaves. The more the bar chart extends downward from level 0, the stronger the signals in cultured cells. The colors of the bars represent the expression patterns observed via SuperSAGE (purple: the same expression levels among samples; red: high expression levels in leaves; orange: high expression levels in cultured cells).

Subsequently, total RNAs were extracted from rice leaves and cultured cells, labeled cRNAs were synthesized therefrom, and the resultants were used as SuperSAGE-Array hybridization probes. As shown in FIG. 3, 7 tags more or less expressed at the same levels between two samples exhibited the same level of hybridization signals between the two samples. The 20 tags more prevalent in leaves actually exhibited stronger hybridization signals in leaf RNA. Among the 14 tags more prevalent in cultured cells, 11 thereof exhibited stronger signals in RNA obtained from cultured cells.

As a result, the results of SuperSAGE analysis of genes and those of SuperSAGE-Array analysis were found to be consistent among 90% or more genes (tags) (38 of 41 tags).

3. SuperSAGE-Array of Non-Model Organism, *Nicotiana benthamiana*

As described above, SuperSAGE is suitable for searching for novel genes of non-model organisms. In order to demonstrate that SuperSAGE-Array is applicable to non-model organisms, a microarray was prepared using 26-bp SuperSAGE tag sequences for genes with expression levels that vary upon overexpression of foreign genes in *Nicotiana benthamiana* leaves, for which no genomic information is available.

The NbCD1 and NbCD3 genes were isolated from *Nicotiana benthamiana* in the past as genes encoding proteins that induce cell death due to overexpression. At the outset, the *Nicotiana benthamiana* genes with expression levels that are increased or decreased upon expression of the NbCD1 and NbCD3 genes were searched for. Agrobacteriums having plasmids of NbCD1, NbCD3, and GFP genes incorporated into the glucocorticoid-inducible expression cassette GVG were introduced into *Nicotiana benthamiana* leaves. Two days after the introduction, the leaves were treated with dexamethasone (DEX) to induce the transgenes to express. RNAs were extracted from the treated leaves 4 hours after DEX treatment and then subjected to SuperSAGE. By comparing SuperSAGE profile, tags that shows more than four-fold representational differences between NbCD1- or NbCD3- and GFP-overexpressing leaves were selected (Tables 2 to 5).

A SuperSAGE-Array upon which the selected tags were immobilized was prepared. In total, 154 types of tags with expression levels that were increased or decreased upon NbCD1 and NbCD3 overexpression were selected for the oligonucleotide array (Tables 2 to 5).

TABLE 2

SuperSAGE tags of genes up-regulated by
NbCD1-overexpression in *N. benthamiana* leaves

| Code | Tag sequence (5'->3') | Number of tags NbCD1-overexpressing | Number of tags GFP-overexpressing | SEQ ID NO: |
|---|---|---|---|---|
| NbCD1U1 | CATGTTGATTATATGACCGGAGGGTA | 7 | 0 | SEQ ID NO: 43 |
| NbCD1U2 | CATGAAGATTATGAGATTGTTTTATC | 5 | 0 | SEQ ID NO: 44 |
| NbCD1U3 | CATGCAAATAAAGTAGTTGTTCGAAA | 5 | 0 | SEQ ID NO: 45 |
| NbCD1U4 | CATGGGCAGTGAAACTGGGAAGAAGA | 6 | 0 | SEQ ID NO: 46 |
| NbCD1U5 | CATGTGGTCTCTCAAATGTTGGAACT | 10 | 0 | SEQ ID NO: 47 |
| NbCD1U6 | CATGTACATTGAAAGATGGAGGCGGA | 13 | 0 | SEQ ID NO: 48 |
| NbCD1U7 | CATGTCTATTGGTTGGCAGGCAAATA | 8 | 0 | SEQ ID NO: 49 |
| NbCD1U8 | CATGAATGAAGTTTGTATCCTCTGTG | 7 | 0 | SEQ ID NO: 50 |
| NbCD1U9 | CATGTTTTCACCCTATATCGATAACC | 7 | 0 | SEQ ID NO: 51 |
| NbCD1U10 | CATGAAGCCATTGGAGGTTTTGTCAC | 6 | 0 | SEQ ID NO: 52 |
| NbCD1U11 | CATGGATCGGCAAACAAAGAGATAAT | 6 | 0 | SEQ ID NO: 53 |
| NbCD1U12 | CATGTATTCATCTGTAAATAGCTTGT | 6 | 0 | SEQ ID NO: 54 |
| NbCD1U13 | CATGTCGTATAAAGTTGTAACGGAGT | 6 | 0 | SEQ ID NO: 55 |
| NbCD1U14 | CATGTTCATTGCCAAGATCTGGACAT | 6 | 0 | SEQ ID NO: 56 |
| NbCD1U15 | CATGAACTTGAAACTATGGATATCTG | 5 | 0 | SEQ ID NO: 57 |
| NbCD1U16 | CATGACTCATATATCAAGTTTATGAG | 5 | 0 | SEQ ID NO: 58 |
| NbCD1U17 | CATGATGCTTGCCAAGTGATGACATT | 5 | 0 | SEQ ID NO: 59 |
| NbCD1U18 | CATGCAAAAATTGTACGTGTGGAAGG | 5 | 0 | SEQ ID NO: 60 |
| NbCD1U19 | CATGTTCTTGTATATGTATCATATGT | 5 | 0 | SEQ ID NO: 61 |
| NbCD1U20 | CATGGCTTCTAGATATCCATATGATG | 34 | 1 | SEQ ID NO: 62 |
| NbCD1U21 | CATGTAGTGCTAAGTAATATTGAATA | 21 | 1 | SEQ ID NO: 63 |
| NbCD1U22 | CATGTAATGTTTTGTTGTACAATATA | 12 | 1 | SEQ ID NO: 64 |
| NbCD1U23 | CATGGTACCATCTTGTTATATTTGGA | 10 | 1 | SEQ ID NO: 65 |
| NbCD1U24 | CATGGTGGTGGGTACATCGTTAGAAG | 9 | 1 | SEQ ID NO: 66 |
| NbCD1U25 | CATGGGCAGATCAATGGGATCCAGCC | 16 | 2 | SEQ ID NO: 67 |
| NbCD1U26 | CATGCCTTTAGTACTTTGGATTTGGG | 8 | 1 | SEQ ID NO: 68 |
| NbCD1U27 | CATGTTACTTGCAACGGCGATAACCA | 8 | 1 | SEQ ID NO: 69 |
| NbCD1U28 | CATGTACCCTGCTGTATATTCGGGAG | 38 | 5 | SEQ ID NO: 70 |
| NbCD1U29 | CATGACGTATTACAAGTACCAAAAGC | 15 | 2 | SEQ ID NO: 71 |
| NbCD1U30 | CATGGATCATATGATTTCATATTTGT | 22 | 3 | SEQ ID NO: 72 |
| NbCD1U31 | CATGGGGTGTTGACCAAGACGCACTT | 7 | 1 | SEQ ID NO: 73 |
| NbCD1U32 | CATGAGTGCAAGCGTTCGAGGTTCCT | 7 | 1 | SEQ ID NO: 74 |
| NbCD1U33 | CATGTCTCATTTTTTGACTGCTGGTT | 13 | 2 | SEQ ID NO: 75 |
| NbCD1U34 | CATGATTACTATTCTATCAAGGGACT | 6 | 1 | SEQ ID NO: 76 |
| NbCD1U35 | CATGTTATGTATGTTTCAGTTGAGAT | 6 | 1 | SEQ ID NO: 77 |
| NbCD1U36 | CATGAGGAAGTTTATGTTACCGGAGA | 11 | 2 | SEQ ID NO: 78 |

TABLE 2-continued

SuperSAGE tags of genes up-regulated by
NbCD1-overexpression in *N. benthamiana* leaves

| Code | Tag sequence (5'->3') | Number of tags | | SEQ ID NO: |
|---|---|---|---|---|
| | | NbCD1-overexpressing | GFP-overexpressing | |
| NbCD1U37 | CATGTTGAGAGACCACCTATTTGTGG | 25 | 5 | SEQ ID NO: 79 |
| NbCD1U38 | CATGCACTAATAATGCTACTTCAAGT | 5 | 0 | SEQ ID NO: 80 |
| NbCD1U39 | CATGTGGAGTTAGATCCAAATTTTCC | 4 | 0 | SEQ ID NO: 81 |
| NbCD1U40 | CATGGTACTACTCCTGGAAGATCATT | 4 | 0 | SEQ ID NO: 82 |
| NbCD1U41 | CATGGATTCCAAAAAAGAGCAAAAGC | 4 | 0 | SEQ ID NO: 83 |
| NbCD1U42 | CATGGATATTGATGATCAGAATAATG | 4 | 0 | SEQ ID NO: 84 |
| NbCD1U43 | CATGCTAATAAGGAAATTGATGCTGC | 4 | 0 | SEQ ID NO: 85 |
| NbCD1U44 | CATGACTTCTTGGGACTGATGTACAT | 4 | 0 | SEQ ID NO: 86 |

TABLE 3

SuperSAGE tags of genes down-regulated by
NbCD1-overexpression in *N. benthamiana* leaves

| Code | Tag sequence (5'->3') | Number of tags | | SEQ ID NO: |
|---|---|---|---|---|
| | | NbCD1-overexpressing | GFP-overexpressing | |
| NbCD1D1 | CATGACTCAAATACTTGTGCACGAGG | 8 | 33 | SEQ ID NO: 87 |
| NbCD1D2 | CATGGCTAATGCTGGACCTGGAACCA | 2 | 10 | SEQ ID NO: 88 |
| NbCD1D3 | CATGCCCCCTTGTGTTATGGAGATCT | 3 | 16 | SEQ ID NO: 89 |
| NbCD1D4 | CATGCGCCCCCCGTCCGCTTGCCGAC | 3 | 16 | SEQ ID NO: 90 |
| NbCD1D5 | CATGAGCAGCTAAGTGAAGAAACTTG | 1 | 6 | SEQ ID NO: 91 |
| NbCD1D6 | CATGATCAAAATAGATTTCAGTTGGG | 1 | 6 | SEQ ID NO: 92 |
| NbCD1D7 | CATGTAATTTCCCAAATCGAACTGTA | 1 | 6 | SEQ ID NO: 93 |
| NbCD1D8 | CATGGACGCTTCCAGACTACACAGGA | 1 | 6 | SEQ ID NO: 94 |
| NbCD1D9 | CATGTATCTGTTATCAACCCTGTGTG | 1 | 6 | SEQ ID NO: 95 |
| NbCD1D10 | CATGGGATTTGGCAGAAGAGGCCCCG | 1 | 8 | SEQ ID NO: 96 |
| NbCD1D11 | CATGGCCCCTGCGCAAGGATGACACG | 2 | 21 | SEQ ID NO: 97 |
| NbCD1D12 | CATGATGAGCTTTAAGGGACTAGTCG | 42 | 442 | SEQ ID NO: 98 |
| NbCD1D13 | CATGGCCGACTTGCTGCACGTCAACC | 1 | 13 | SEQ ID NO: 99 |
| NbCD1D14 | CATGATAAGCTTTAAGGGATTAGTCG | 1 | 20 | SEQ ID NO: 100 |
| NbCD1D15 | CATGATGCAGCTGGGTTGTGATGGCG | 0 | 5 | SEQ ID NO: 101 |
| NbCD1D16 | CATGCGCCGTTTTGGCTGTAGAATGG | 0 | 7 | SEQ ID NO: 102 |
| NbCD1D17 | CATGTAATGTATGCAAGTTGTTGCTA | 0 | 7 | SEQ ID NO: 103 |
| NbCD1D18 | CATGGACAATTTGGTTAGGTTCAGCT | 0 | 5 | SEQ ID NO: 104 |
| NbCD1D19 | CATGACCGTGGAGCCTTGATCATTTT | 0 | 7 | SEQ ID NO: 105 |
| NbCD1D20 | CATGGATAGTCCTTCACATTGGCACG | 0 | 7 | SEQ ID NO: 106 |
| NbCD1D21 | CATGCCAGCTGGGAGAGCTAATCCGC | 0 | 6 | SEQ ID NO: 107 |
| NbCD1D22 | CATGGGCGTGACCGTGGGAATGGAGG | 0 | 6 | SEQ ID NO: 108 |

TABLE 3-continued

SuperSAGE tags of genes down-regulated by
NbCD1-overexpression in N. benthamiana leaves

| Code | Tag sequence (5'->3') | NbCD1-overexpressing | GFP-overexpressing | SEQ ID NO: |
|---|---|---|---|---|
| NbCD1D23 | CATGGGGGTATACCACACTGTCTTTG | 0 | 6 | SEQ ID NO: 109 |
| NbCD1D24 | CATGGGACTTGGTGGATGCATTGCTC | 0 | 5 | SEQ ID NO: 110 |
| NbCD1D25 | CATGGTGACGAAGCCAGATTGGTGGC | 0 | 5 | SEQ ID NO: 111 |
| NbCD1D26 | CATGTGCTGCAGGCAGTGCTTCCGCA | 0 | 5 | SEQ ID NO: 112 |
| NbCD1D27 | CATGTGAAAGAACAGACTGAGCTTGT | 0 | 5 | SEQ ID NO: 113 |
| NbCD1D28 | CATGGATGGTATGTGCCTGCTCCAGT | 0 | 5 | SEQ ID NO: 114 |
| NbCD1D29 | CATGCAAAACACTCTCATCCCCCCTA | 0 | 4 | SEQ ID NO: 115 |
| NbCD1D30 | CATGGAGGCATTCTCCCGTACGTCAT | 0 | 4 | SEQ ID NO: 116 |
| NbCD1D31 | CATGTCTACGGAGGCTGTAACTTTTT | 0 | 4 | SEQ ID NO: 117 |
| NbCD1D32 | CATGGGTAGAGCCAAAGAGTGTGAAC | 0 | 4 | SEQ ID NO: 118 |
| NbCD1D33 | CATGTTCTGCTACTCGACTATGAGAC | 0 | 4 | SEQ ID NO: 119 |
| NbCD1D34 | CATGTGCTTCAAGACGTATCACTTGT | 0 | 4 | SEQ ID NO: 120 |
| NbCD1D35 | CATGTACACTTCAAGAATCCTACTCC | 0 | 4 | SEQ ID NO: 121 |
| NbCD1D36 | CATGGGTAGATGGATGGTTTGCTTAG | 0 | 4 | SEQ ID NO: 122 |
| NbCD1D37 | CATGGCACAGTTAAAGGATTCTCTCT | 0 | 4 | SEQ ID NO: 123 |
| NbCD1D38 | CATGGATGAAGAAGCTGCTGGGTTTT | 0 | 4 | SEQ ID NO: 124 |
| NbCD1D39 | CATGACACGGTCAAGCAAAGATCTGT | 0 | 4 | SEQ ID NO: 125 |

TABLE 4

SuperSAGE tags of genes up-regulated by
NbCD3-overexpression in N. benthamiana leaves

| Code | Tag sequence (5'->3') | NbCD3-overexpressing | GFP-overexpressing | SEQ ID NO: |
|---|---|---|---|---|
| NbCD3U1 | CATGTGCAGGACTTTAGATCCTTGCA | 54 | 1 | SEQ ID NO:126 |
| NbCD3U2 | CATGTTGTATAAAGTTGTAACGAAGC | 13 | 1 | SEQ ID NO:127 |
| NbCD3U3 | CATGATTTTATGGTAACTTGATTGAT | 9 | 1 | SEQ ID NO:128 |
| NbCD3U4 | CATGTTTACCCTTTGACGGCCCAAAT | 9 | 1 | SEQ ID NO:129 |
| NbCD3U5 | CATGCATAACAATACATTTTGGTCAT | 8 | 1 | SEQ ID NO:130 |
| NbCD3U6 | CATGCCTTCTTTTCTTTGTATTATCA | 8 | 1 | SEQ ID NO:131 |
| NbCD3U7 | CATGGATTAACATCATTATTCTCTGT | 8 | 0 | SEQ ID NO:132 |
| NbCD3U8 | CATGACACTGATAACTGCCGAGGATT | 7 | 1 | SEQ ID NO:133 |
| NbCD3U9 | CATGATAACGTTTATCTAAGAAGAGG | 7 | 1 | SEQ ID NO:134 |
| NbCD3U10 | CATGGATGGAAAACTTAGTACCAATA | 7 | 1 | SEQ ID NO:135 |
| NbCD3U11 | CATGTGAAAGAACAGACCGAGCTTGT | 7 | 1 | SEQ ID NO:136 |
| NbCD3U12 | CATGAAGTCCATCAAAGTCCTAGGCT | 7 | 0 | SEQ ID NO:137 |

TABLE 4-continued

SuperSAGE tags of genes up-regulated by
NbCD3-overexpression in N. benthamiana leaves

| Code | Tag sequence (5'->3') | Number of tags | | SEQ ID NO: |
| --- | --- | --- | --- | --- |
| | | NbCD3-overexpressing | GFP-overexpressing | |
| NbCD3U13 | CATGATCATTCTTTTGTATACCGTGT | 7 | 0 | SEQ ID NO:138 |
| NbCD3U14 | CATGTTTGGAGTAATTCTCCTTGTAT | 7 | 0 | SEQ ID NO:139 |
| NbCD3U15 | CATGGCATCTCTTGACAATGTTGGGG | 6 | 1 | SEQ ID NO:140 |
| NbCD3U16 | CATGGTCCTTCAAGGGGAAGCAGGTG | 6 | 1 | SEQ ID NO:141 |
| NbCD3U17 | CATGTAAGGAGTGCTACTGAAATGGA | 6 | 1 | SEQ ID NO:142 |
| NbCD3U18 | CATGTGGTCTCTCAAATGTTGGAACT | 6 | 1 | SEQ ID NO:143 |
| NbCD3U19 | CATGTTGAACCTCTGTAATTCCGATC | 6 | 1 | SEQ ID NO:144 |
| NbCD3U20 | CATGAACACAACTAGAGTGAAGAAGT | 6 | 0 | SEQ ID NO:145 |
| NbCD3U21 | CATGAAGTTATACGCCGGACTAAAGT | 6 | 0 | SEQ ID NO:146 |
| NbCD3U22 | CATGAATGAATTTAACAGTTCAATAT | 6 | 0 | SEQ ID NO:147 |
| NbCD3U23 | CATGATAGGATAACAAAGATATATAT | 6 | 0 | SEQ ID NO:148 |
| NbCD3U24 | CATGCCTTTAGTACTTTGGATTTGGG | 6 | 0 | SEQ ID NO:149 |
| NbCD3U25 | CATGGATCGGCAAACAAAGAGATAAT | 6 | 0 | SEQ ID NO:150 |
| NbCD3U26 | CATGTTAAAGTGAAACGCAACAATGG | 6 | 0 | SEQ ID NO:151 |
| NbCD3U27 | CATGTTGATTATATGACCGGAGGGTA | 6 | 0 | SEQ ID NO:152 |
| NbCD3U28 | CATGACGAAGTTCCAACACGAAGAGA | 5 | 0 | SEQ ID NO:153 |
| NbCD3U29 | CATGATAAATGGGAGACCCTTGTACT | 5 | 0 | SEQ ID NO:154 |
| NbCD3U30 | CATGATCATTTTCCTGAGATTCGACG | 5 | 0 | SEQ ID NO:155 |
| NbCD3U31 | CATGCAAAACCTAAAATAACCAAACT | 5 | 0 | SEQ ID NO:156 |
| NbCD3U32 | CATGGAGTTGTATCTTGACTGCTTCT | 5 | 0 | SEQ ID NO:157 |
| NbCD3U33 | CATGGGATAGCTTTTCATCTTTGGAT | 5 | 0 | SEQ ID NO:158 |
| NbGD3U34 | CATGTAACCATACAAGTTGAACCATC | 5 | 0 | SEQ ID NO:159 |
| NbCD3U35 | CATGTGAATGACGCAAACTTTCAAGT | 5 | 0 | SEQ ID NO:160 |
| NbCD3U36 | CATGTTATAGTATGAGATAGAGGAGT | 5 | 0 | SEQ ID NO:161 |
| NbCD3U37 | CATGTCCCTGTTTGTATGTTCTGTT | 35 | 7 | SEQ ID NO:162 |
| NbCD3U38 | CATGGAGCTACAGGACTTCATTCTCC | 18 | 2 | SEQ ID NO:163 |
| NbCD3U39 | CATGATCTCTTTCCTGAGATTCGTCA | 16 | 2 | SEQ ID NO:164 |
| NbCD3U40 | CATGGGCAGATCAATGGGATCCAGCC | 13 | 3 | SEQ ID NO:165 |
| NbCD3U41 | CATGGAAGAAGCAACCTTAGTGTGGT | 11 | 2 | SEQ ID NO:166 |
| NbCD3U42 | CATGTGGAATGTTCGTATTGTGAATA | 9 | 2 | SEQ ID NO:167 |

TABLE 5

SuperSAGE tags of genes down-regulated by
NbCD3-overexpression in *N. benthamiana* leaves

| Code | Tag sequence (5'->3') | Number of tags NbCD3-overexpressing | Number of tags GFP-overexpressing | SEQ ID NO: |
|---|---|---|---|---|
| NbCD3D1 | CATGTTGCTGAAGTTTTCACGGGTGC | 1 | 12 | SEQ ID NO: 168 |
| NbCD3D2 | CATGCAAGGCCAGTCGGAGAAGAAGG | 1 | 8 | SEQ ID NO: 169 |
| NbCD3D3 | CATGAGGGATGAGCCAGGAGCACGGC | 1 | 7 | SEQ ID NO: 170 |
| NbCD3D4 | CATGTTGCAACTTCTAGTCAATGACT | 1 | 7 | SEQ ID NO: 171 |
| NbCD3D5 | CATGAGCGGAAGCTAACCTGAATCCA | 1 | 6 | SEQ ID NO: 172 |
| NbCD3D6 | CATGCCTGTGAGCCTGCTGTTGGTAA | 1 | 6 | SEQ ID NO: 173 |
| NbCD3D7 | CATGGCACCAGCGTGGAATGTCGCAT | 1 | 6 | SEQ ID NO: 174 |
| NbCD3D8 | CATGGGGATATAGCAAGATCGTGAAT | 1 | 6 | SEQ ID NO: 175 |
| NbCD3D9 | CATGTTATCTTTCCAATAGAGGCGAG | 0 | 6 | SEQ ID NO: 176 |
| NbCD3D10 | CATGAGACTCTAAACAATTTCGCTTG | 0 | 5 | SEQ ID NO: 177 |
| NbCD3D11 | CATGCAGCAAAGACCAAGAACAGCCC | 0 | 5 | SEQ ID NO: 178 |
| NbGD3D12 | CATGCCGAAGCAAATCCACGAAATCA | 0 | 5 | SEQ ID NO: 179 |
| NbCD3D13 | CATGCTTACAAAGGGAATCCAGCTAC | 0 | 5 | SEQ ID NO: 180 |
| NbCD3D14 | CATGGGGTCTCCCGCTGGTAAGGTAT | 0 | 5 | SEQ ID NO: 181 |
| NbCD3D15 | CATGACGCGCTTAACCTACACTCTTG | 1 | 5 | SEQ ID NO: 182 |
| NbCD3D16 | CATGAGGAGGCTAGAAGGAAGAATGT | 1 | 5 | SEQ ID NO: 183 |
| NbCD3D17 | CATGAGGGATGAACCAGGAGCCAGAC | 1 | 5 | SEQ ID NO: 184 |
| NbCD3D18 | CATGATTTGTAACTATTGGGGATTCT | 1 | 5 | SEQ ID NO: 185 |
| NbCD3D19 | CATGGATATATGGCAATTGCGTTTGT | 1 | 5 | SEQ ID NO: 186 |
| NbCD3D20 | CATGGGTGCTGAGATGGTTTAATGGT | 1 | 5 | SEQ ID NO: 187 |
| NbCD3D21 | CATGTAATTTGGCGGGAGTAATGTA | 1 | 5 | SEQ ID NO: 188 |
| NbCD3D22 | CATGAATAAATGCTACTCTAATAGCT | 0 | 4 | SEQ ID NO: 189 |
| NbCD3D23 | CATGACGGAAAAGCCAATTATCAAGT | 0 | 4 | SEQ ID NO: 190 |
| NbCD3D24 | CATGATTGGGCAATTTGGTGTTGGTT | 0 | 4 | SEQ ID NO: 191 |
| NbCD3D25 | CATGATTTTCAAGGACGGAGAGAAGA | 0 | 4 | SEQ ID NO: 192 |
| NbCD3D26 | CATGCCACCGGGGTCCACAACGTGCT | 0 | 4 | SEQ ID NO: 193 |
| NbCD3D27 | CATGCTGCCCAACTTTGTGTATTGGC | 0 | 4 | SEQ ID NO: 194 |
| NbCD3D28 | CATGGGTTTCAGCTTGTTTGATTAAG | 0 | 4 | SEQ ID NO: 195 |
| NbCD3D29 | CATGTATAAATTGTGTAATGTTGTGT | 0 | 4 | SEQ ID NO: 196 |

Figure 4:
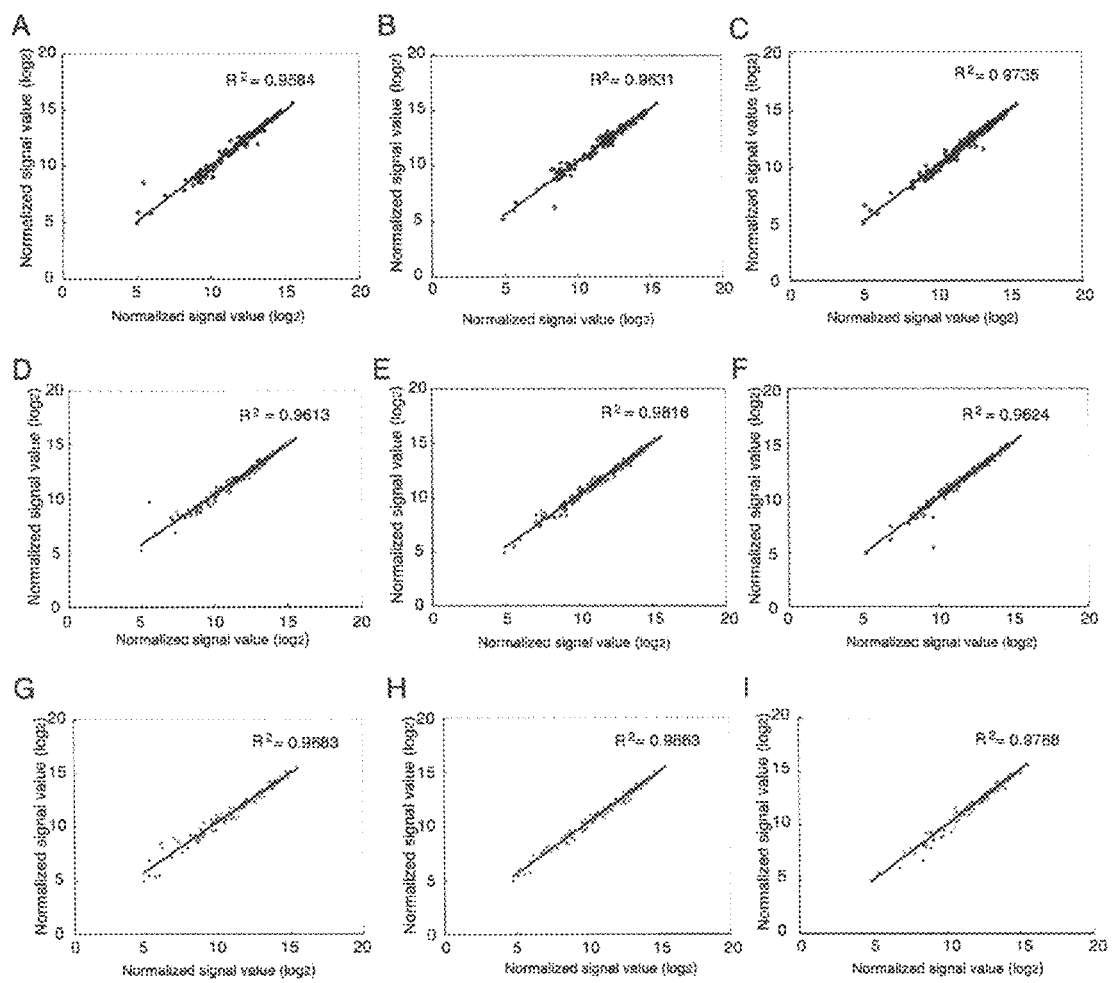
FIG. 4 shows charts representing the reproducibility of a SuperSAGE-Array of foreign gene-overexpressing Nicotiana benthamiana leaves.

RNAs were extracted from leaves overexpressing GFP, NbCD1, and NbCD3 for hybridization to the arrays. Gene overexpression and hybridization were independently triplicated. In order to observe reproducibility among hybridization triplicates, the signal values of hybridization of the tags to the oligos were plotted between two arrays. Satisfactory correlations were observed in most signal values among the triplicates ($R^2$=0.9584 to 0.9863). Thus, the array involving the use of the SuperSAGE tags yielded the results of hybridization with very high reproducibility (FIG. 4).

The average signal values of genes among the triplicates are shown in Tables 6 to 9. Based on the differences in average signal values among the GFP-overexpressing leaves and the NbCD1- or NbCD3-overexpressing leaves, gene expression patterns were analyzed using Cluster and TreeView software and indicated by color tiles (FIG. 5). Based on the results of SuperSAGE-Array analysis, genes were classified as follows: (A) genes induced upon NbCD1 overexpression; (B) genes repressed upon NbCD1 overexpression; (C) genes induced upon NbCD3 overexpression; and (D) genes repressed upon NbCD3 overexpression. Compared with the control GFP-overexpressing leaves, stronger signals are indicated by red tiles and weaker signals are indicated by green tiles. SuperSAGE tags starting from NbCD1U and NbCD3U generally exhibited stronger hybridization signals than the control upon overexpression of the genes. Many tags with lowered expression levels (SuperSAGE tags starting from NbCD1D and NbCD3D) emitted the signals weaker than those of the control. The genes exhibiting statistically significant differences in expression levels were selected. As a result, 115 genes (i.e., 74% of the genes subjected to array analysis) were found to exhibit the same expression patterns between SuperSAGE and SuperSAGE-Array analysis (Table 10).

TABLE 6

Average of normalized hybridization signal values ($Log_2$) of down-regulated genes in NbCD1-overexpressing *N. benthamiana* leaves.

| Code | GFP-overexpressing | s.e. (±)* | NbCD1-overexpressing | s.e. (±)* |
|---|---|---|---|---|
| NbCD1D1 | 14.445 | 0.155 | 14.197 | 0.045 |
| NbCD1D2 | 14.684 | 0.072 | 14.325 | 0.010 |
| NbCD1D3 | 14.025 | 0.111 | 13.549 | 0.050 |
| NbCD1D4 | 13.212 | 0.197 | 12.654 | 0.214 |
| NbCD1D5 | 10.779 | 0.164 | 9.727 | 0.131 |
| NbCD1D6 | 9.406 | 0.329 | 8.888 | 0.113 |
| NbCD1D7 | 8.019 | 0.465 | 7.168 | 0.294 |
| NbCD1D8 | 12.916 | 0.042 | 12.284 | 0.085 |
| NbCD1D9 | 13.187 | 0.078 | 12.643 | 0.029 |
| NbCD1D10 | 11.379 | 0.041 | 10.269 | 0.229 |
| NbCD1D11 | 13.119 | 0.119 | 11.859 | 0.208 |
| NbCD1D12 | 14.943 | 0.053 | 6.893 | 2.392 |
| NbCD1D13 | 13.945 | 0.103 | 13.387 | 0.094 |
| NbCD1D14 | 12.539 | 0.135 | 4.981 | 0.138 |
| NbCD1D15 | 13.637 | 0.042 | 12.390 | 0.040 |
| NbCD1D16 | 12.631 | 0.084 | 11.639 | 0.138 |
| NbCD1D17 | 12.881 | 0.070 | 11.731 | 0.133 |
| NbCD1D18 | 14.231 | 0.086 | 12.898 | 0.059 |
| NbCD1D19 | 13.159 | 0.089 | 12.696 | 0.050 |
| NbCD1D20 | 13.157 | 0.186 | 8.078 | 0.105 |
| NbCD1D21 | 9.424 | 0.212 | 10.261 | 0.106 |
| NbCD1D22 | 12.751 | 0.075 | 11.439 | 0.133 |
| NbCD1D23 | 13.481 | 0.099 | 12.874 | 0.088 |
| NbCD1D24 | 12.077 | 0.077 | 11.983 | 0.099 |
| NbCD1D25 | 11.270 | 0.169 | 10.919 | 0.244 |
| NbCD1D26 | 12.649 | 0.131 | 11.824 | 0.113 |
| NbCD1D27 | 9.903 | 0.221 | 10.040 | 0.350 |
| NbCD1D28 | 11.677 | 0.046 | 11.190 | 0.100 |
| NbCD1D29 | 9.702 | 0.177 | 9.474 | 0.176 |
| NbCD1D30 | 12.901 | 0.186 | 12.469 | 0.074 |
| NbCD1D31 | 12.757 | 0.061 | 12.581 | 0.068 |
| NbCD1D32 | 10.435 | 0.067 | 10.242 | 0.075 |
| NbCD1D33 | 13.756 | 0.188 | 13.072 | 0.067 |
| NbCD1D34 | 12.270 | 0.407 | 11.441 | 0.204 |
| NbCD1D35 | 12.549 | 0.093 | 12.230 | 0.031 |
| NbCD1D36 | 13.547 | 0.084 | 12.782 | 0.141 |
| NbCD1D37 | 12.171 | 0.224 | 11.228 | 0.098 |
| NbCD1D38 | 10.725 | 0.078 | 10.489 | 0.193 |
| NbCD1D39 | 10.679 | 0.220 | 10.212 | 0.219 |

*s.e.: standard error of hybridization signal values among triplicates

TABLE 7

Average of normalized hybridization signal values ($Log_2$) of up-regulated genes in NbCD1-overexpressing *N. benthamiana* leaves.

| Code | GFP-overexpressing | s.e. (±)* | NbCD1-overexpressing | s.e. (±)* |
|---|---|---|---|---|
| NbCD1U1 | 11.720 | 0.211 | 12.782 | 0.178 |
| NbCD1U2 | 10.172 | 0.250 | 10.657 | 0.286 |
| NbCD1U3 | 9.832 | 0.264 | 10.618 | 0.117 |
| NbCD1U4 | 7.317 | 0.424 | 10.930 | 0.266 |

TABLE 7-continued

Average of normalized hybridization signal values ($Log_2$) of up-regulated genes in NbCD1-overexpressing *N. benthamiana* leaves.

| Code | GFP-overexpressing | s.e. (±)* | NbCD1-overexpressing | s.e. (±)* |
|---|---|---|---|---|
| NbCD1U5 | 12.605 | 0.239 | 14.723 | 0.121 |
| NbCD1U6 | 5.868 | 0.134 | 8.038 | 0.320 |
| NbCD1U7 | 12.541 | 0.471 | 13.220 | 0.054 |
| NbCD1U8 | 10.133 | 0.214 | 12.282 | 0.079 |
| NbCD1U9 | 13.298 | 0.031 | 12.967 | 0.172 |
| NbCD1U10 | 11.078 | 0.359 | 12.868 | 0.168 |
| NbCD1U11 | 9.350 | 0.321 | 12.087 | 0.056 |
| NbCD1U12 | 11.416 | 0.164 | 13.622 | 0.011 |
| NbCD1U13 | 10.792 | 0.632 | 12.961 | 0.082 |
| NbCD1U14 | 10.915 | 0.657 | 13.801 | 0.089 |
| NbCD1U15 | 11.116 | 0.196 | 10.891 | 0.127 |
| NbCD1U16 | 9.173 | 0.631 | 10.456 | 0.274 |
| NbCD1U17 | 13.097 | 0.043 | 13.207 | 0.046 |
| NbCD1U18 | 9.439 | 0.308 | 9.102 | 0.332 |
| NbCD1U19 | 12.771 | 0.139 | 12.682 | 0.136 |
| NbCD1U20 | 6.713 | 1.561 | 14.696 | 0.033 |
| NbCD1U21 | 12.697 | 0.219 | 12.343 | 0.143 |
| NbCD1U22 | 11.009 | 0.400 | 10.514 | 0.199 |
| NbCD1U23 | 13.180 | 0.106 | 14.073 | 0.058 |
| NbCD1U24 | 8.835 | 0.073 | 8.540 | 0.193 |
| NbCD1U25 | 11.836 | 0.073 | 13.783 | 0.066 |
| NbCD1U26 | 13.396 | 0.192 | 14.108 | 0.033 |
| NbCD1U27 | 14.279 | 0.046 | 14.041 | 0.031 |
| NbCD1U28 | 14.016 | 0.138 | 14.535 | 0.057 |
| NbCD1U29 | 12.828 | 0.118 | 12.927 | 0.114 |
| NbCD1U30 | 12.245 | 0.486 | 12.802 | 0.103 |
| NbCD1U31 | 12.153 | 0.102 | 11.250 | 0.108 |
| NbCD1U32 | 12.322 | 0.320 | 12.377 | 0.075 |
| NbCD1U33 | 13.703 | 0.126 | 13.134 | 0.026 |
| NbCD1U34 | 12.472 | 0.081 | 11.700 | 0.208 |
| NbCD1U35 | 13.573 | 0.103 | 13.936 | 0.088 |
| NbCD1U36 | 11.067 | 0.377 | 13.365 | 0.228 |
| NbCD1U37 | 13.720 | 0.193 | 14.212 | 0.079 |
| NbCD1U38 | 12.383 | 0.232 | 13.318 | 0.166 |
| NbCD1U39 | 11.440 | 0.257 | 13.267 | 0.162 |
| NbCD1U40 | 12.229 | 0.295 | 13.174 | 0.141 |
| NbCD1U41 | 5.027 | 0.102 | 6.302 | 0.459 |
| NbCD1U42 | 11.551 | 0.165 | 12.399 | 0.034 |
| NbCD1U43 | 8.999 | 0.227 | 11.510 | 0.456 |
| NbCD1U44 | 11.776 | 0.403 | 13.154 | 0.238 |

*s.e.: standard error of hybridization signal values among triplicates

TABLE 8

Average of normalized hybridization signal values ($Log_2$) of up-regulated genes in NbCD3-overexpressing *N. benthamiana* leaves.

| Code | GFP-overexpressing | s.e. (±)* | NbCD3-overexpressing | s.e. (±)* |
|---|---|---|---|---|
| NbCD3U1 | 9.338 | 0.334 | 14.490 | 0.069 |
| NbCD3U2 | 12.419 | 0.353 | 12.565 | 0.082 |
| NbCD3U3 | 8.884 | 0.637 | 11.439 | 0.227 |
| NbCD3U4 | 13.347 | 0.301 | 14.981 | 0.159 |
| NbCD3U5 | 12.751 | 0.146 | 13.141 | 0.157 |
| NbCD3U6 | 14.025 | 0.107 | 13.136 | 0.211 |
| NbCD3U7 | 13.749 | 0.058 | 13.902 | 0.078 |
| NbCD3U8 | 12.551 | 0.109 | 12.843 | 0.065 |
| NbCD3U9 | 9.076 | 0.312 | 8.941 | 0.311 |
| NbCD3U10 | 12.798 | 0.166 | 13.198 | 0.103 |
| NbCD3U11 | 10.615 | 0.165 | 11.848 | 0.162 |
| NbCD3U12 | 10.763 | 0.071 | 12.675 | 0.172 |
| NbCD3U13 | 12.230 | 0.161 | 14.141 | 0.099 |
| NbCD3U14 | 8.062 | 0.241 | 11.898 | 0.058 |
| NbCD3U15 | 12.525 | 0.114 | 13.191 | 0.123 |
| NbCD3U16 | 12.984 | 0.105 | 12.718 | 0.097 |
| NbCD3U17 | 12.185 | 0.325 | 12.912 | 0.087 |
| NbCD3U18 | 12.562 | 0.276 | 14.760 | 0.137 |
| NbCD3U19 | 13.088 | 0.183 | 12.979 | 0.043 |

TABLE 8-continued

Average of normalized hybridization signal values (Log$_2$) of up-regulated genes in NbCD3-overexpressing *N. benthamiana* leaves.

| Code | GFP-overexpressing | s.e. (±)* | NbCD3-overexpressing | s.e. (±)* |
|---|---|---|---|---|
| NbCD3U20 | 9.771 | 0.720 | 11.138 | 0.494 |
| NbCD3U21 | 14.115 | 0.124 | 14.200 | 0.013 |
| NbCD3U22 | 9.706 | 0.178 | 9.153 | 0.510 |
| NbCD3U23 | 5.852 | 0.775 | 7.893 | 0.035 |
| NbCD3U24 | 13.342 | 0.240 | 14.523 | 0.108 |
| NbCD3U25 | 9.324 | 0.303 | 11.114 | 0.113 |
| NbCD3U26 | 9.034 | 0.373 | 8.762 | 0.296 |
| NbCD3U27 | 11.796 | 0.431 | 12.485 | 0.048 |
| NbCD3U28 | 9.631 | 0.044 | 10.643 | 0.138 |
| NbCD3U29 | 9.212 | 0.278 | 8.617 | 0.538 |
| NbCD3U30 | 12.251 | 0.863 | 12.282 | 0.259 |
| NbCD3U31 | 9.597 | 0.476 | 10.945 | 0.124 |
| NbCD3U32 | 13.710 | 0.091 | 13.316 | 0.092 |
| NbCD3U33 | 14.235 | 0.022 | 13.831 | 0.056 |
| NbCD3U34 | 11.909 | 0.037 | 12.893 | 0.086 |
| NbCD3U35 | 9.288 | 0.371 | 10.428 | 0.097 |
| NbCD3U36 | 8.824 | 0.350 | 5.991 | 0.770 |
| NbCD3U37 | 14.771 | 0.071 | 14.944 | 0.118 |
| NbCD3U38 | 14.398 | 0.048 | 14.898 | 0.061 |
| NbCD3U39 | 13.079 | 0.142 | 13.771 | 0.155 |
| NbCD3U40 | 11.950 | 0.183 | 13.631 | 0.219 |
| NbCD3U41 | 12.915 | 0.061 | 12.482 | 0.046 |
| NbCD3U42 | 13.335 | 0.075 | 13.618 | 0.077 |

*s.e.: standard error of hybridization signal values among triplicates

TABLE 9

Average of normalized hybridization signal values (Log2) of down-regulated genes in NbCD3-overexpressing *N. benthamiana* leaves.

| Code | GFP-overexpressing | s.e. (±)* | NbCD3-overexpressing | s.e. (±)* |
|---|---|---|---|---|
| NbCD3D1 | 13.757 | 0.041 | 13.526 | 0.078 |
| NbCD3D2 | 9.681 | 0.227 | 9.267 | 0.354 |
| NbCD3D3 | 9.764 | 0.136 | 9.593 | 0.108 |
| NbCD3D4 | 11.050 | 0.049 | 7.876 | 0.974 |
| NbCD3D5 | 12.010 | 0.081 | 11.401 | 0.146 |
| NbCD3D6 | 13.409 | 0.169 | 13.066 | 0.103 |
| NbCD3D7 | 12.111 | 0.118 | 11.423 | 0.111 |
| NbCD3D8 | 11.656 | 0.175 | 11.003 | 0.198 |
| NbCD3D9 | 13.842 | 0.041 | 13.691 | 0.051 |
| NbCD3D10 | 12.116 | 0.174 | 10.371 | 0.490 |
| NbCD3D11 | 10.711 | 0.212 | 9.166 | 0.426 |
| NbCD3D12 | 12.084 | 0.180 | 11.681 | 0.123 |
| NbCD3D13 | 10.922 | 0.174 | 10.314 | 0.223 |
| NbCD3D14 | 12.254 | 0.209 | 12.172 | 0.076 |
| NbCD3D15 | 12.308 | 0.040 | 9.585 | 0.642 |
| NbCD3D16 | 8.563 | 0.211 | 8.537 | 0.189 |
| NbCD3D17 | 9.126 | 0.069 | 8.974 | 0.121 |
| NbCD3D18 | 12.063 | 0.023 | 10.389 | 0.333 |
| NbCD3D19 | 12.362 | 0.440 | 10.202 | 0.520 |
| NbCD3D20 | 11.170 | 0.148 | 11.055 | 0.152 |
| NbCD3D21 | 9.823 | 0.328 | 7.940 | 0.545 |
| NbCD3D22 | 10.923 | 0.265 | 10.084 | 0.371 |
| NbCD3D23 | 10.983 | 0.018 | 10.623 | 0.074 |
| NbCD3D24 | 13.841 | 0.098 | 13.156 | 0.120 |
| NbCD3D25 | 10.456 | 0.218 | 7.949 | 0.719 |
| NbCD3D26 | 9.331 | 0.305 | 11.180 | 0.285 |
| NbCD3D27 | 12.287 | 0.079 | 11.673 | 0.023 |
| NbCD3D28 | 14.425 | 0.070 | 14.136 | 0.061 |
| NbCD3D29 | 11.301 | 0.162 | 10.357 | 0.118 |

*s.e.: standard error of hybridization signal values among triplicates

TABLE 10

|  | NbCD1 overexpression | | NbCD3 overexpression | | |
|---|---|---|---|---|---|
|  | Increased | Decreased | Increased | Decreased | Total |
| SuperSAGE | 46 | 39 | 42 | 29 | 156 |
| SuperSAGE-Array | 32 | 33 | 28 | 22 | 115 |

4. Discussion

The SuperSAGE-Array system developed by the present inventors directly employed 26-bp tags without optimizing the Tm value. This analysis, however, yielded highly reproducible results. This indicates that a SuperSAGE-Array can be applied to: 1) evaluation of SuperSAGE results; and 2) gene expression analysis of multiple samples detected by SuperSAGE.

A SuperSAGE-Array does not require the designing of oligo probes. Thus, an array can be prepared 1 to 1.5 months after the SuperSAGE analysis, and extensive gene expression analysis can be carried out. Specifically, the SuperSAGE-Array is an excellent tool that enables precise analysis of genes identified by SuperSAGE.

Some tags did not yield the results that were consistent between SuperSAGE and SuperSAGE-Array for the following reasons. That is, such tags were located in the vicinity of a poly(A) sequence, hybridization was not satisfactorily carried out, or 26-bp probes hybridized to RNAs of the homologous genes. Such problems may be overcome by performing SuperSAGE analysis using a different anchoring enzyme.

In this example, specific tags were extracted using a restriction enzyme, NlaIII, which recognizes a 4-nucleotide sequence. Instead of NlaIII, a restriction enzyme, such as Sau3AI, may be used to extract the same tags. By using a SuperSAGE-Array for all the tags of interest in two libraries, hybridization may be satisfactorily carried out with at least 1 oligonucleotide of the gene identified by SuperSAGE.

Example 2

In Example 1, model rice plants were subjected to expression analysis using an array with 41 SuperSAGE tags immobilized thereon, and non-model *Nicotiana benthamiana* plants were subjected to expression analysis using an array with 154 SuperSAGE tags immobilized thereon. In both cases, the results of analysis were very consistent with the results of expression analysis via SuperSAGE. In this example, an array with 1,000 SuperSAGE tags immobilized thereon was prepared for rice, and the results of expression analysis via SuperSAGE-Array were compared with those via SuperSAGE.

In accordance with the procedure of Example 1, mRNAs were extracted from rice leaves (variety: Yashiromochi) and cultured cells of rice (variety: Kakehashi) to prepare SuperSAGE libraries. From these libraries, 1,000 SuperSAGE tag sequences were selected. Among them, 78 tags represented equally expressed genes, 438 tags were more prevalent in leaves and 484 tags were more abundant in suspension-cultured cells. Based on the determined tag sequences, arrays were prepared using the 12-well array system (NimbleScreen 12: NimbleGen Co.). For the tag sequences, mismatch-containing oligonucleotides, wherein nucleotides 7 and 13 were modified (heterogeneous sequences), were synthesized and used for a hybridization specificity test.

Total RNAs were extracted from rice leaves and cultured cells, Cy3-labeled cRNAs were synthesized, and the resultants were used as hybridization probes. The probes were allowed to hybridize to the prepared array, the signals were read with a scanner, and the data was standardized by the Robust Multi-chip Analysis (RMA) method. Hybridization was independently triplicated. In order to observe reproducibility among hybridization triplicates, the hybridization signal values of the tags were plotted between two arrays. As a result, satisfactory correlations were observed in most signal values among the triplicates ($R^2$=0.973 to 0.992), as with the case of Example 1. Array preparation and hybridization were entrusted to Gene Frontier.

Figure 6:
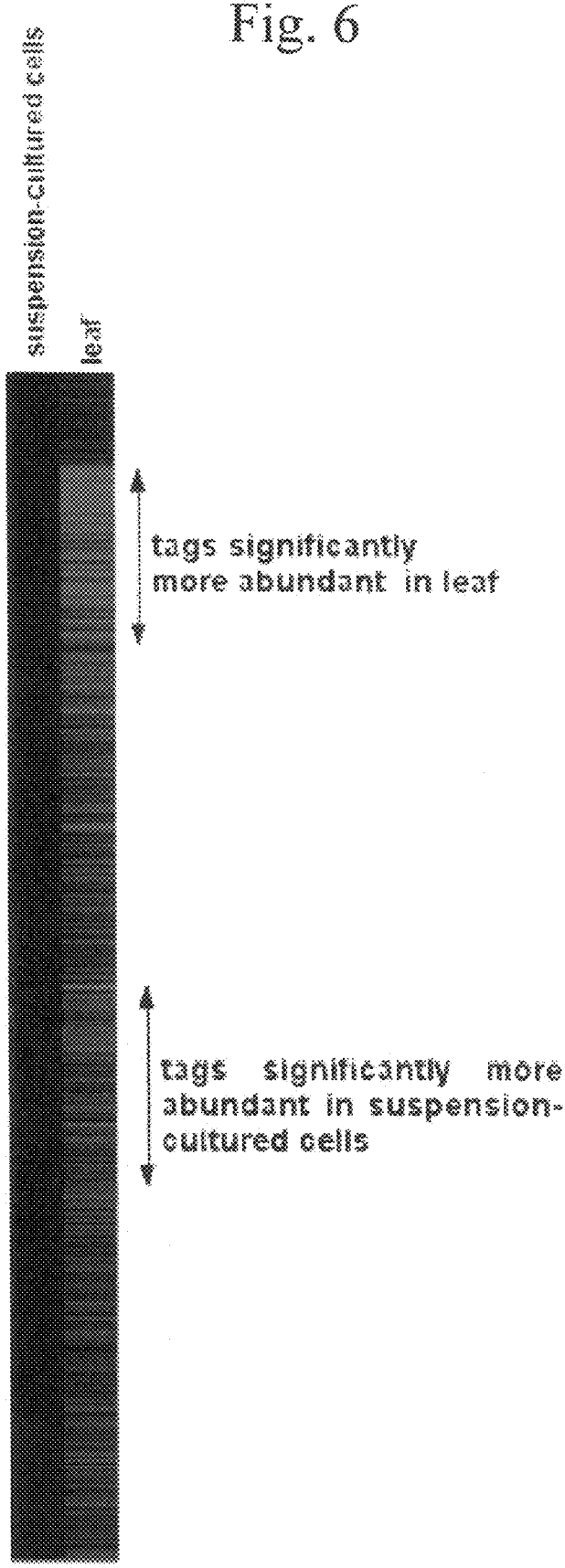
FIG. 6 shows the results of SuperSAGE-Array analysis of differences in the gene expression profiles between rice leaves and cultured cells. Expression levels that were higher in leaves than in cultured cells are indicated by red tiles, and those that were higher in cultured cells than in leaves are indicated by green tiles.

FIG. 6 shows the expression patterns of genes in rice leaves and in cultured cells observed via SuperSAGE-Array. Table 11 shows a comparison of the results of expression analysis via SuperSAGE-Array and via SuperSAGE.

TABLE 11

Gene expression in rice leaves and in cultured cells
Comparison of results of gene expression analysis via
SuperSAGE-Array and via SuperSAGE

| | Genes expressed at high level in leaves | | Genes expressed at high level in cultured cells | |
| --- | --- | --- | --- | --- |
| | With significant difference ($p < 0.05$) | Whole | With significant difference ($p < 0.05$) | Whole |
| SuperSAGE | 155 | 438 | 167 | 484 |
| SuperSAGE-Array | 136 | 352 | 149 | 421 |
| Consistency (%)* | (87.7) | (80.4) | (89.2) | (87.0) |

*Level of consistency between the results of expression analysis via SuperSAGE-Array and via SuperSAGE As a result, the gene group with a detected expression level that was higher in leaves than in cultured cells was found to exhibit a consistency of 80.4% (87.7% for those exhibiting statistic significance) between SuperSAGE and SuperSAGE-Array. The gene group with a detected expression level that was higher in cultured cells than in leaves was found to exhibit a consistency of 87.0% (89.2% for those exhibiting statistic significance) therebetween.

Example 3

Among the tags that were found to be expressed at high levels in all of the NbCD1- and NbCD3-overexpressing *Nicotiana benthamiana* leaves by the SuperSAGE-Array-based expression analysis in Example 1, 5 tags showing no sequence matches to known cDNA or EST were selected (NbCD3U14, 20, 25, 32, and 40), and identification of the genes corresponding thereto was attempted.

Figure 7:
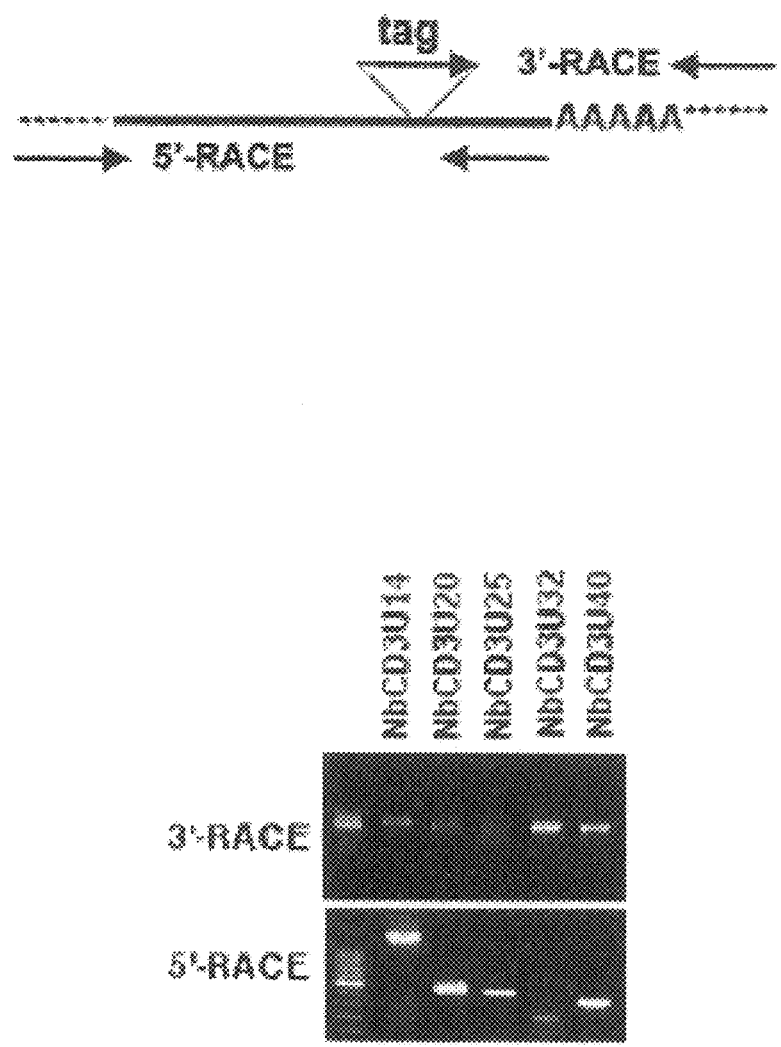
FIG. 7 schematically shows the amplification of full-length sequences corresponding to 5 tags derived from Nicotiana benthamiana (NbCD3U14, 20, 25, 32, and 40) by the 3'-RACE and 5'-RACE methods (upper portion) and the results of electrophoresis of the PCR products thereof (lower portion).

Full-length sequences of the tags were determined by the 3'-RACE and 5'-RACE methods in the following manner. As a template, RNA was isolated from NbCD3-overexpressing *Nicotiana benthamiana* leaves, and the RNA was flanked by adaptor sequences to synthesize cDNA. Based on the SuperSAGE tag sequences, a gene specific PCR primer and a primer complementary to the adaptor sequence were used to amplify a partial cDNA fragment from template cDNA. A primer was prepared based on the 5'-sequence of the resulting fragment, and the resulting primer and the adaptor primer (i.e., a primer complementary to the adaptor sequence) were used to amplify the upstream region. FIG. 7 schematically shows the amplification of full-length sequences by the 3'-RACE and 5'-RACE methods (upper portion) and the results of electrophoresis of the PCR products thereof (lower portion).

The results of the 3'-RACE method were combined with those of the 5'-RACE method to determine the full-length sequences of the genes corresponding to the 5 tags. It was confirmed that the SuperSAGE tag sequences were mapped at expected positions in all 5 genes. Functions of these genes can be deduced from the putative ORFs and the results of BLAST search. The results of SuperSAGE-Array-based analysis demonstrated that full-length sequences of unknown genes could be easily determined and that functions thereof could be easily deduced.

Thus, the SuperSAGE-Array was found to be unique and effective, providing the advantages of highly quantitative SAGE in combination with those of high-throughput microarray systems.

INDUSTRIAL APPLICABILITY

According to the present invention, oligoarrays of any tissues or genes expressed under desired conditions can be easily prepared. For example, SuperSAGE-Arrays of various cancer tissues are useful for clinical testing, and SuperSAGE-Arrays can be applied to all eukaryotic organisms. Also, SuperSAGE-Arrays upon which host organism and pathogen genes are spotted can be applied to host-pathogen interaction analysis. Thus, the present invention can be applied to gene expression analysis in any field, including applications ranging from the basic to the clinical.

All publications, patents, and patent applications cited herein are incorporated herein by reference in their entirety.
Sequence Listing Free Text
SEQ ID NO: 8; oligo-dT primer
SEQ ID NO: 197; linker A sequence
SEQ ID NO: 198; linker A sequence
SEQ ID NO: 199; linker B sequence
SEQ ID NO: 200; linker B sequence

The invention claimed is:

1. A method of preparing an array of oligonucleotides comprising
   (a) immobilizing oligonucleotide tags each comprising an oligonucleotide of more than 25 bp for identifying expressed genes on a solid support, wherein the oligonucleotide tags comprise nucleotide sequences determined by the following steps:
      1) synthesizing at least one cDNA pool from mRNAs of expressed genes using a primer comprising a recognition sequence of a type III restriction enzyme and an oligo-dT sequence, and treating the cDNA pool with a second restriction enzyme;
      2) purifying a poly(A)-containing fragment from the cDNA pool, and dividing the purified poly(A)-containing fragment such that some of the fragment is ligated to a linker A and some of the fragment is ligated to a linker B;
      3) treating the fragments with the type III restriction enzyme, and ligating the resulting linker A-containing fragment to the resulting linker B-containing fragment;
      4) removing linker sequences by cleaving the ligated fragments with the second restriction enzyme to obtain ditag oligonucleotides, wherein each ditag oligonucleotide contains two individual tags;
      5) ligating ditag oligonucleotides to each other to prepare polynucleotides;
      6) analyzing the nucleotide sequences of the above polynucleotides to determine the nucleotide sequences of tags contained in the polynucleotides;
      7) analyzing the frequency of occurrence of individual tags among the sequenced polynucleotides; and
      8) selecting individual tags based on their frequency; and
   (b) immobilizing control oligonucleotide tags on the solid support, wherein the control oligonucleotide tags comprise nucleotide sequences of the selected tags with two-base mismatches in positions 7 and 13.

2. The method according to claim 1, wherein the type III restriction enzyme is EcoP15I.

3. The method according to claim 1, wherein the second restriction enzyme is any of NlaIII, Hsp92II, FatI, BfaI, MaeI, XspI, HpyCH4IV, MaeII, TaiI, TscI, AluI, TaqI, BfuCI, Bsp143I, BstENII, DpnII, Kzo9I, MboI, NdeII, Sau3AI, BstKTI, or Csp6I.

4. The method according to claim 1, wherein linker A and linker B are double-stranded DNAs different from each other and are obtained by annealing the following first strand of DNA (1) and second strand of DNA (2)

DNA (1): 5'-N$_{30\text{-}40}$-CAGCAGCATG-3'

DNA (2): 3'-N$_{30\text{-}40}$-GTCGTC-5' wherein "N$_{30\text{-}40}$" of DNA (1) is complementary to "N$_{30\text{-}40}$" of DNA (2) and each thereof is a sequence comprising 30 to 40 arbitrary nucleotides.

5. The method according to claim 1, wherein the oligonucleotide tags are synthesized on the solid support or the oligonucleotide tags are pre-synthesized prior to being immobilizing on the solid support.

6. The method according to claim 4, wherein the 5'-end of DNA (1) is labeled, and the 3'-end of DNA (2) is amino-modified.

7. The method according to claim 1, comprising two cDNA pools, wherein each pool is synthesized from mRNAs of the same genes expressed (a) under different conditions, (b) in different tissues, or (c)(i) in wildtype cells and (ii) in recombinant cells or mutant cells.

8. The method according to claim 7, wherein individual tags are selected because the frequency of their occurrence differs depending on the cDNA pool used to prepare the polynucleotides that are sequenced.

9. The method according to claim 7, wherein individual tags are selected because the frequency of their occurrence is substantially the same in the polynucleotides prepared from both cDNA pools.

10. A method of preparing an array of oligonucleotides comprising:
   (a) immobilizing oligonucleotide tags each comprising an oligonucleotide of more than 25 bp for identifying expressed genes on a solid support, wherein the oligonucleotide tags comprise nucleotide sequences determined by the following steps:
      1) synthesizing at least one cDNA pool from mRNAs of expressed genes using a primer comprising a recognition sequence of a type III restriction enzyme and an oligo-dT sequence, and treating the cDNA pool with a second restriction enzyme;
      2) purifying a poly(A)-containing fragment from the cDNA pool, and dividing the purified poly(A)-containing fragment such that some of the fragment is ligated to a linker A and some of the fragment is ligated to a linker B;
      3) treating the fragments with the type III restriction enzyme, and ligating the resulting linker A-containing fragment to the resulting linker B-containing fragment;
      4) removing linker sequences by cleaving the ligated fragments with the second restriction enzyme to obtain ditag oligonucleotides, wherein each ditag oligonucleotide contains two individual tags;
      5) analyzing the frequency of occurrence of individual tags among the ditag oligonucleotides;
      6) selecting individual tags based on their frequency; and
      7) analyzing the nucleotide sequences of the selected tags; and
   (b) immobilizing control oligonucleotide tags on the solid support, wherein the control oligonucleotide tags comprise nucleotide sequences of the selected tags with two-base mismatches in positions 7 and 13.

* * * * *

SEQUENCE LISTING

```
<160> NUMBER OF SEQ ID NOS: 211

<210> SEQ ID NO 1
<211> LENGTH: 26
<212> TYPE: DNA
<213> ORGANISM: Oryza sativa

<400> SEQUENCE: 1
catgaattga gttcgctttg gttatg                                        26
```

```
<210> SEQ ID NO 2
<211> LENGTH: 26
<212> TYPE: DNA
<213> ORGANISM: Oryza sativa

<400> SEQUENCE: 2
catggtttgg ttggattagg cggagt                                              26

<210> SEQ ID NO 3
<211> LENGTH: 26
<212> TYPE: DNA
<213> ORGANISM: Oryza sativa

<400> SEQUENCE: 3
catgggctaa agccagccaa actggt                                              26

<210> SEQ ID NO 4
<211> LENGTH: 26
<212> TYPE: DNA
<213> ORGANISM: Oryza sativa

<400> SEQUENCE: 4
catgtcggtt cagttatgtg aacttg                                              26

<210> SEQ ID NO 5
<211> LENGTH: 26
<212> TYPE: DNA
<213> ORGANISM: Oryza sativa

<400> SEQUENCE: 5
catgtaatgt ttgctatcgt gagtta                                              26

<210> SEQ ID NO 6
<211> LENGTH: 26
<212> TYPE: DNA
<213> ORGANISM: Oryza sativa

<400> SEQUENCE: 6
catggctgac ccagccttcc gtccac                                              26

<210> SEQ ID NO 7
<211> LENGTH: 26
<212> TYPE: DNA
<213> ORGANISM: Oryza sativa

<400> SEQUENCE: 7
catgggagcg actccgtgga caacgg                                              26

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence: Synthetic
      oligo dT primer

<400> SEQUENCE: 8
ctgatctaga ggtaccggat cccagcagtt tttttttttt tttttt                        47

<210> SEQ ID NO 9
<211> LENGTH: 26
<212> TYPE: DNA
<213> ORGANISM: Oryza sativa

<400> SEQUENCE: 9
```

-continued

```
catgttcggc tgcaccgatg ccaccc                                        26

<210> SEQ ID NO 10
<211> LENGTH: 26
<212> TYPE: DNA
<213> ORGANISM: Oryza sativa

<400> SEQUENCE: 10
catggggacg catcgccttc agctaa                                        26

<210> SEQ ID NO 11
<211> LENGTH: 26
<212> TYPE: DNA
<213> ORGANISM: Oryza sativa

<400> SEQUENCE: 11
catgtaatat gatgcctaga gcatat                                        26

<210> SEQ ID NO 12
<211> LENGTH: 26
<212> TYPE: DNA
<213> ORGANISM: Oryza sativa

<400> SEQUENCE: 12
catgtaatgg tacatatctc cttgtt                                        26

<210> SEQ ID NO 13
<211> LENGTH: 26
<212> TYPE: DNA
<213> ORGANISM: Oryza sativa

<400> SEQUENCE: 13
catgctcaag atgatcgagg actacc                                        26

<210> SEQ ID NO 14
<211> LENGTH: 26
<212> TYPE: DNA
<213> ORGANISM: Oryza sativa

<400> SEQUENCE: 14
catgtatgta tgtcccttaa ttgtgt                                        26

<210> SEQ ID NO 15
<211> LENGTH: 26
<212> TYPE: DNA
<213> ORGANISM: Oryza sativa

<400> SEQUENCE: 15
catgttgata ttgtatcagc aagcac                                        26

<210> SEQ ID NO 16
<211> LENGTH: 26
<212> TYPE: DNA
<213> ORGANISM: Oryza sativa

<400> SEQUENCE: 16
catggacgag cgcgacgcca agatcc                                        26

<210> SEQ ID NO 17
<211> LENGTH: 26
<212> TYPE: DNA
<213> ORGANISM: Oryza sativa

<400> SEQUENCE: 17
```

```
catggcgcag gaggtgcttc tcggcg                                        26
```

<210> SEQ ID NO 18
<211> LENGTH: 26
<212> TYPE: DNA
<213> ORGANISM: Oryza sativa

<400> SEQUENCE: 18

```
catgtactac taccttgtaa actttt                                        26
```

<210> SEQ ID NO 19
<211> LENGTH: 26
<212> TYPE: DNA
<213> ORGANISM: Oryza sativa

<400> SEQUENCE: 19

```
catgttcggg tgcactgacg ccaccc                                        26
```

<210> SEQ ID NO 20
<211> LENGTH: 26
<212> TYPE: DNA
<213> ORGANISM: Oryza sativa

<400> SEQUENCE: 20

```
catggggat tgtgcacgca tctggc                                         26
```

<210> SEQ ID NO 21
<211> LENGTH: 26
<212> TYPE: DNA
<213> ORGANISM: Oryza sativa

<400> SEQUENCE: 21

```
catgtgtgta cgtggtgtgt tttgag                                        26
```

<210> SEQ ID NO 22
<211> LENGTH: 26
<212> TYPE: DNA
<213> ORGANISM: Oryza sativa

<400> SEQUENCE: 22

```
catgcataat tgaacgcttg tcgtgc                                        26
```

<210> SEQ ID NO 23
<211> LENGTH: 26
<212> TYPE: DNA
<213> ORGANISM: Oryza sativa

<400> SEQUENCE: 23

```
catgtgtaaa tactgccgtg tgtttc                                        26
```

<210> SEQ ID NO 24
<211> LENGTH: 26
<212> TYPE: DNA
<213> ORGANISM: Oryza sativa

<400> SEQUENCE: 24

```
catggatccg tctctctggg aggaat                                        26
```

<210> SEQ ID NO 25
<211> LENGTH: 26
<212> TYPE: DNA
<213> ORGANISM: Oryza sativa

<400> SEQUENCE: 25

-continued catgtcggac aagtgcggca actgcg                                    26

<210> SEQ ID NO 26
<211> LENGTH: 26
<212> TYPE: DNA
<213> ORGANISM: Oryza sativa

<400> SEQUENCE: 26
catgtggtgg cttagctcta cgtgta                                    26

<210> SEQ ID NO 27
<211> LENGTH: 26
<212> TYPE: DNA
<213> ORGANISM: Oryza sativa

<400> SEQUENCE: 27
catgttgtaa tactccatca aagagt                                    26

<210> SEQ ID NO 28
<211> LENGTH: 26
<212> TYPE: DNA
<213> ORGANISM: Oryza sativa

<400> SEQUENCE: 28
catgcatatg tgaatgctag caccag                                    26

<210> SEQ ID NO 29
<211> LENGTH: 26
<212> TYPE: DNA
<213> ORGANISM: Oryza sativa

<400> SEQUENCE: 29
catgtgctgt tgtggcgtgt cgctag                                    26

<210> SEQ ID NO 30
<211> LENGTH: 26
<212> TYPE: DNA
<213> ORGANISM: Oryza sativa

<400> SEQUENCE: 30
catgcttcaa tatatatcca tcaaat                                    26

<210> SEQ ID NO 31
<211> LENGTH: 26
<212> TYPE: DNA
<213> ORGANISM: Oryza sativa

<400> SEQUENCE: 31
catggatttg cactgtctga tctatc                                    26

<210> SEQ ID NO 32
<211> LENGTH: 26
<212> TYPE: DNA
<213> ORGANISM: Oryza sativa

<400> SEQUENCE: 32
catgcacaac agcacaagtg gagtag                                    26

<210> SEQ ID NO 33
<211> LENGTH: 26
<212> TYPE: DNA
<213> ORGANISM: Oryza sativa

<400> SEQUENCE: 33
catggtaatg taccaaacag cgatga    26

<210> SEQ ID NO 34
<211> LENGTH: 26
<212> TYPE: DNA
<213> ORGANISM: Oryza sativa

<400> SEQUENCE: 34
catgcgtttg tgggcaagaa gacaat    26

<210> SEQ ID NO 35
<211> LENGTH: 26
<212> TYPE: DNA
<213> ORGANISM: Oryza sativa

<400> SEQUENCE: 35
catgctggta gctcagcgaa tctcct    26

<210> SEQ ID NO 36
<211> LENGTH: 26
<212> TYPE: DNA
<213> ORGANISM: Oryza sativa

<400> SEQUENCE: 36
catggcacgg ttacccgtca tttccg    26

<210> SEQ ID NO 37
<211> LENGTH: 26
<212> TYPE: DNA
<213> ORGANISM: Oryza sativa

<400> SEQUENCE: 37
catgatgatg gccgccaccg ccaccg    26

<210> SEQ ID NO 38
<211> LENGTH: 26
<212> TYPE: DNA
<213> ORGANISM: Oryza sativa

<400> SEQUENCE: 38
catgcgagtt cccggggctc aagatc    26

<210> SEQ ID NO 39
<211> LENGTH: 26
<212> TYPE: DNA
<213> ORGANISM: Oryza sativa

<400> SEQUENCE: 39
catggccacc gctaccaacg gcaacg    26

<210> SEQ ID NO 40
<211> LENGTH: 26
<212> TYPE: DNA
<213> ORGANISM: Oryza sativa

<400> SEQUENCE: 40
catggtcgcc gccgccgtgc cggagc    26

<210> SEQ ID NO 41
<211> LENGTH: 26
<212> TYPE: DNA
<213> ORGANISM: Oryza sativa

<400> SEQUENCE: 41

```
catgtgtgtt gtgtgtacga tgagct                                    26

<210> SEQ ID NO 42
<211> LENGTH: 26
<212> TYPE: DNA
<213> ORGANISM: Oryza sativa

<400> SEQUENCE: 42
catgttaagt ttgagatatg atatga                                    26

<210> SEQ ID NO 43
<211> LENGTH: 26
<212> TYPE: DNA
<213> ORGANISM: Nicotiana benthamiana

<400> SEQUENCE: 43
catgttgatt atatgaccgg agggta                                    26

<210> SEQ ID NO 44
<211> LENGTH: 26
<212> TYPE: DNA
<213> ORGANISM: Nicotiana benthamiana

<400> SEQUENCE: 44
catgaagatt atgagattgt tttatc                                    26

<210> SEQ ID NO 45
<211> LENGTH: 26
<212> TYPE: DNA
<213> ORGANISM: Nicotiana benthamiana

<400> SEQUENCE: 45
catgcaaata aagtagttgt tcgaaa                                    26

<210> SEQ ID NO 46
<211> LENGTH: 26
<212> TYPE: DNA
<213> ORGANISM: Nicotiana benthamiana

<400> SEQUENCE: 46
catgggcagt gaaactggga agaaga                                    26

<210> SEQ ID NO 47
<211> LENGTH: 26
<212> TYPE: DNA
<213> ORGANISM: Nicotiana benthamiana

<400> SEQUENCE: 47
catgtggtct ctcaaatgtt ggaact                                    26

<210> SEQ ID NO 48
<211> LENGTH: 26
<212> TYPE: DNA
<213> ORGANISM: Nicotiana benthamiana

<400> SEQUENCE: 48
catgtacatt gaaagatgga ggcgga                                    26

<210> SEQ ID NO 49
<211> LENGTH: 26
<212> TYPE: DNA
<213> ORGANISM: Nicotiana benthamiana

<400> SEQUENCE: 49
```

```
catgtctatt ggttggcagg caaata                                          26
```

<210> SEQ ID NO 50
<211> LENGTH: 26
<212> TYPE: DNA
<213> ORGANISM: Nicotiana benthamiana

<400> SEQUENCE: 50

```
catgaatgaa gtttgtatcc tctgtg                                          26
```

<210> SEQ ID NO 51
<211> LENGTH: 26
<212> TYPE: DNA
<213> ORGANISM: Nicotiana benthamiana

<400> SEQUENCE: 51

```
catgttttca ccctatatcg ataacc                                          26
```

<210> SEQ ID NO 52
<211> LENGTH: 26
<212> TYPE: DNA
<213> ORGANISM: Nicotiana benthamiana

<400> SEQUENCE: 52

```
catgaagcca ttggaggttt tgtcac                                          26
```

<210> SEQ ID NO 53
<211> LENGTH: 26
<212> TYPE: DNA
<213> ORGANISM: Nicotiana benthamiana

<400> SEQUENCE: 53

```
catggatcgg caaacaaaga gataat                                          26
```

<210> SEQ ID NO 54
<211> LENGTH: 26
<212> TYPE: DNA
<213> ORGANISM: Nicotiana benthamiana

<400> SEQUENCE: 54

```
catgtattca tctgtaaata gcttgt                                          26
```

<210> SEQ ID NO 55
<211> LENGTH: 26
<212> TYPE: DNA
<213> ORGANISM: Nicotiana benthamiana

<400> SEQUENCE: 55

```
catgtcgtat aaagttgtaa cggagt                                          26
```

<210> SEQ ID NO 56
<211> LENGTH: 26
<212> TYPE: DNA
<213> ORGANISM: Nicotiana benthamiana

<400> SEQUENCE: 56

```
catgttcatt gccaagatct ggacat                                          26
```

<210> SEQ ID NO 57
<211> LENGTH: 26
<212> TYPE: DNA
<213> ORGANISM: Nicotiana benthamiana

<400> SEQUENCE: 57

```
catgaacttg aaactatgga tatctg                                          26

<210> SEQ ID NO 58
<211> LENGTH: 26
<212> TYPE: DNA
<213> ORGANISM: Nicotiana benthamiana

<400> SEQUENCE: 58
catgactcat atatcaagtt tatgag                                          26

<210> SEQ ID NO 59
<211> LENGTH: 26
<212> TYPE: DNA
<213> ORGANISM: Nicotiana benthamiana

<400> SEQUENCE: 59
catgatgctt gccaagtgat gacatt                                          26

<210> SEQ ID NO 60
<211> LENGTH: 26
<212> TYPE: DNA
<213> ORGANISM: Nicotiana benthamiana

<400> SEQUENCE: 60
catgcaaaaa ttgtacgtgt ggaagg                                          26

<210> SEQ ID NO 61
<211> LENGTH: 26
<212> TYPE: DNA
<213> ORGANISM: Nicotiana benthamiana

<400> SEQUENCE: 61
catgttcttg tatatgtatc atatgt                                          26

<210> SEQ ID NO 62
<211> LENGTH: 26
<212> TYPE: DNA
<213> ORGANISM: Nicotiana benthamiana

<400> SEQUENCE: 62
catggcttct agatatccat atgatg                                          26

<210> SEQ ID NO 63
<211> LENGTH: 26
<212> TYPE: DNA
<213> ORGANISM: Nicotiana benthamiana

<400> SEQUENCE: 63
catgtagtgc taagtaatat tgaata                                          26

<210> SEQ ID NO 64
<211> LENGTH: 26
<212> TYPE: DNA
<213> ORGANISM: Nicotiana benthamiana

<400> SEQUENCE: 64
catgtaatgt tttgttgtac aatata                                          26

<210> SEQ ID NO 65
<211> LENGTH: 26
<212> TYPE: DNA
<213> ORGANISM: Nicotiana benthamiana

<400> SEQUENCE: 65
```

```
catggtacca tcttgttata tttgga                                    26

<210> SEQ ID NO 66
<211> LENGTH: 26
<212> TYPE: DNA
<213> ORGANISM: Nicotiana benthamiana

<400> SEQUENCE: 66
catggtggtg ggtacatcgt tagaag                                    26

<210> SEQ ID NO 67
<211> LENGTH: 26
<212> TYPE: DNA
<213> ORGANISM: Nicotiana benthamiana

<400> SEQUENCE: 67
catgggcaga tcaatgggat ccagcc                                    26

<210> SEQ ID NO 68
<211> LENGTH: 26
<212> TYPE: DNA
<213> ORGANISM: Nicotiana benthamiana

<400> SEQUENCE: 68
catgccttta gtactttgga tttggg                                    26

<210> SEQ ID NO 69
<211> LENGTH: 26
<212> TYPE: DNA
<213> ORGANISM: Nicotiana benthamiana

<400> SEQUENCE: 69
catgttactt gcaacggcga taacca                                    26

<210> SEQ ID NO 70
<211> LENGTH: 26
<212> TYPE: DNA
<213> ORGANISM: Nicotiana benthamiana

<400> SEQUENCE: 70
catgtaccct gctgtatatt cgggag                                    26

<210> SEQ ID NO 71
<211> LENGTH: 26
<212> TYPE: DNA
<213> ORGANISM: Nicotiana benthamiana

<400> SEQUENCE: 71
catgacgtat tacaagtacc aaaagc                                    26

<210> SEQ ID NO 72
<211> LENGTH: 26
<212> TYPE: DNA
<213> ORGANISM: Nicotiana benthamiana

<400> SEQUENCE: 72
catggatcat atgatttcat atttgt                                    26

<210> SEQ ID NO 73
<211> LENGTH: 26
<212> TYPE: DNA
<213> ORGANISM: Nicotiana benthamiana

<400> SEQUENCE: 73
```

```
catggggtgt tgaccaagac gcactt                                          26

<210> SEQ ID NO 74
<211> LENGTH: 26
<212> TYPE: DNA
<213> ORGANISM: Nicotiana benthamiana

<400> SEQUENCE: 74
catgagtgca agcgttcgag gttcct                                          26

<210> SEQ ID NO 75
<211> LENGTH: 26
<212> TYPE: DNA
<213> ORGANISM: Nicotiana benthamiana

<400> SEQUENCE: 75
catgtctcat tttttgactg ctggtt                                          26

<210> SEQ ID NO 76
<211> LENGTH: 26
<212> TYPE: DNA
<213> ORGANISM: Nicotiana benthamiana

<400> SEQUENCE: 76
catgattact attctatcaa gggact                                          26

<210> SEQ ID NO 77
<211> LENGTH: 26
<212> TYPE: DNA
<213> ORGANISM: Nicotiana benthamiana

<400> SEQUENCE: 77
catgttatgt atgtttcagt tgagat                                          26

<210> SEQ ID NO 78
<211> LENGTH: 26
<212> TYPE: DNA
<213> ORGANISM: Nicotiana benthamiana

<400> SEQUENCE: 78
catgaggaag tttatgttac cggaga                                          26

<210> SEQ ID NO 79
<211> LENGTH: 26
<212> TYPE: DNA
<213> ORGANISM: Nicotiana benthamiana

<400> SEQUENCE: 79
catgttgaga gaccacctat ttgtgg                                          26

<210> SEQ ID NO 80
<211> LENGTH: 26
<212> TYPE: DNA
<213> ORGANISM: Nicotiana benthamiana

<400> SEQUENCE: 80
catgcactaa taatgctact tcaagt                                          26

<210> SEQ ID NO 81
<211> LENGTH: 26
<212> TYPE: DNA
<213> ORGANISM: Nicotiana benthamiana

<400> SEQUENCE: 81
```

```
catgtggagt tagatccaaa tttttcc                                           26

<210> SEQ ID NO 82
<211> LENGTH: 26
<212> TYPE: DNA
<213> ORGANISM: Nicotiana benthamiana

<400> SEQUENCE: 82
catggtacta ctcctggaag atcatt                                           26

<210> SEQ ID NO 83
<211> LENGTH: 26
<212> TYPE: DNA
<213> ORGANISM: Nicotiana benthamiana

<400> SEQUENCE: 83
catggattcc aaaaaagagc aaaagc                                           26

<210> SEQ ID NO 84
<211> LENGTH: 26
<212> TYPE: DNA
<213> ORGANISM: Nicotiana benthamiana

<400> SEQUENCE: 84
catggatatt gatgatcaga ataatg                                           26

<210> SEQ ID NO 85
<211> LENGTH: 26
<212> TYPE: DNA
<213> ORGANISM: Nicotiana benthamiana

<400> SEQUENCE: 85
catgctaata aggaaattga tgctgc                                           26

<210> SEQ ID NO 86
<211> LENGTH: 26
<212> TYPE: DNA
<213> ORGANISM: Nicotiana benthamiana

<400> SEQUENCE: 86
catgacttct tgggactgat gtacat                                           26

<210> SEQ ID NO 87
<211> LENGTH: 26
<212> TYPE: DNA
<213> ORGANISM: Nicotiana benthamiana

<400> SEQUENCE: 87
catgactcaa atacttgtgc acgagg                                           26

<210> SEQ ID NO 88
<211> LENGTH: 26
<212> TYPE: DNA
<213> ORGANISM: Nicotiana benthamiana

<400> SEQUENCE: 88
catggctaat gctggacctg gaacca                                           26

<210> SEQ ID NO 89
<211> LENGTH: 26
<212> TYPE: DNA
<213> ORGANISM: Nicotiana benthamiana

<400> SEQUENCE: 89
```

```
catgcccct tgtgttatgg agatct                                    26

<210> SEQ ID NO 90
<211> LENGTH: 26
<212> TYPE: DNA
<213> ORGANISM: Nicotiana benthamiana

<400> SEQUENCE: 90
catgcgcccc ccgtccgctt gccgac                                   26

<210> SEQ ID NO 91
<211> LENGTH: 26
<212> TYPE: DNA
<213> ORGANISM: Nicotiana benthamiana

<400> SEQUENCE: 91
catgagcagc taagtgaaga aacttg                                   26

<210> SEQ ID NO 92
<211> LENGTH: 26
<212> TYPE: DNA
<213> ORGANISM: Nicotiana benthamiana

<400> SEQUENCE: 92
catgatcaaa atagatttca gttggg                                   26

<210> SEQ ID NO 93
<211> LENGTH: 26
<212> TYPE: DNA
<213> ORGANISM: Nicotiana benthamiana

<400> SEQUENCE: 93
catgtaattt cccaaatcga actgta                                   26

<210> SEQ ID NO 94
<211> LENGTH: 26
<212> TYPE: DNA
<213> ORGANISM: Nicotiana benthamiana

<400> SEQUENCE: 94
catggacgct tccagactac acagga                                   26

<210> SEQ ID NO 95
<211> LENGTH: 26
<212> TYPE: DNA
<213> ORGANISM: Nicotiana benthamiana

<400> SEQUENCE: 95
catgtatctg ttatcaaccc tgtgtg                                   26

<210> SEQ ID NO 96
<211> LENGTH: 26
<212> TYPE: DNA
<213> ORGANISM: Nicotiana benthamiana

<400> SEQUENCE: 96
catgggattt ggcagaagag gccccg                                   26

<210> SEQ ID NO 97
<211> LENGTH: 26
<212> TYPE: DNA
<213> ORGANISM: Nicotiana benthamiana

<400> SEQUENCE: 97
```

```
catggcccct gcgcaaggat gacacg                                    26

<210> SEQ ID NO 98
<211> LENGTH: 26
<212> TYPE: DNA
<213> ORGANISM: Nicotiana benthamiana

<400> SEQUENCE: 98
catgatgagc tttaagggac tagtcg                                    26

<210> SEQ ID NO 99
<211> LENGTH: 26
<212> TYPE: DNA
<213> ORGANISM: Nicotiana benthamiana

<400> SEQUENCE: 99
catggccgac ttgctgcacg tcaacc                                    26

<210> SEQ ID NO 100
<211> LENGTH: 26
<212> TYPE: DNA
<213> ORGANISM: Nicotiana benthamiana

<400> SEQUENCE: 100
catgataagc tttaagggat tagtcg                                    26

<210> SEQ ID NO 101
<211> LENGTH: 26
<212> TYPE: DNA
<213> ORGANISM: Nicotiana benthamiana

<400> SEQUENCE: 101
catgatgcag ctgggttgtg atggcg                                    26

<210> SEQ ID NO 102
<211> LENGTH: 26
<212> TYPE: DNA
<213> ORGANISM: Nicotiana benthamiana

<400> SEQUENCE: 102
catgcgccgt tttggctgta gaatgg                                    26

<210> SEQ ID NO 103
<211> LENGTH: 26
<212> TYPE: DNA
<213> ORGANISM: Nicotiana benthamiana

<400> SEQUENCE: 103
catgtaatgt atgcaagttg ttgcta                                    26

<210> SEQ ID NO 104
<211> LENGTH: 26
<212> TYPE: DNA
<213> ORGANISM: Nicotiana benthamiana

<400> SEQUENCE: 104
catggacaat ttggttaggt tcagct                                    26

<210> SEQ ID NO 105
<211> LENGTH: 26
<212> TYPE: DNA
<213> ORGANISM: Nicotiana benthamiana

<400> SEQUENCE: 105
```

```
catgaccgtg gagccttgat catttt                                          26

<210> SEQ ID NO 106
<211> LENGTH: 26
<212> TYPE: DNA
<213> ORGANISM: Nicotiana benthamiana

<400> SEQUENCE: 106
catggatagt ccttcacatt ggcacg                                          26

<210> SEQ ID NO 107
<211> LENGTH: 26
<212> TYPE: DNA
<213> ORGANISM: Nicotiana benthamiana

<400> SEQUENCE: 107
catgccagct gggagagcta atccgc                                          26

<210> SEQ ID NO 108
<211> LENGTH: 26
<212> TYPE: DNA
<213> ORGANISM: Nicotiana benthamiana

<400> SEQUENCE: 108
catgggcgtg accgtgggaa tggagg                                          26

<210> SEQ ID NO 109
<211> LENGTH: 26
<212> TYPE: DNA
<213> ORGANISM: Nicotiana benthamiana

<400> SEQUENCE: 109
catgggggta taccacactg tctttg                                          26

<210> SEQ ID NO 110
<211> LENGTH: 26
<212> TYPE: DNA
<213> ORGANISM: Nicotiana benthamiana

<400> SEQUENCE: 110
catgggactt ggtggatgca ttgctc                                          26

<210> SEQ ID NO 111
<211> LENGTH: 26
<212> TYPE: DNA
<213> ORGANISM: Nicotiana benthamiana

<400> SEQUENCE: 111
catggtgacg aagccagatt ggtggc                                          26

<210> SEQ ID NO 112
<211> LENGTH: 26
<212> TYPE: DNA
<213> ORGANISM: Nicotiana benthamiana

<400> SEQUENCE: 112
catgtgctgc aggcagtgct tccgca                                          26

<210> SEQ ID NO 113
<211> LENGTH: 26
<212> TYPE: DNA
<213> ORGANISM: Nicotiana benthamiana

<400> SEQUENCE: 113
```
catgtgaaag aacagactga gcttgt                                          26

<210> SEQ ID NO 114
<211> LENGTH: 26
<212> TYPE: DNA
<213> ORGANISM: Nicotiana benthamiana

<400> SEQUENCE: 114
catggatggt atgtgcctgc tccagt                                          26

<210> SEQ ID NO 115
<211> LENGTH: 26
<212> TYPE: DNA
<213> ORGANISM: Nicotiana benthamiana

<400> SEQUENCE: 115
catgcaaaac actctcatcc ccccta                                          26

<210> SEQ ID NO 116
<211> LENGTH: 26
<212> TYPE: DNA
<213> ORGANISM: Nicotiana benthamiana

<400> SEQUENCE: 116
catggaggca ttctcccgta cgtcat                                          26

<210> SEQ ID NO 117
<211> LENGTH: 26
<212> TYPE: DNA
<213> ORGANISM: Nicotiana benthamiana

<400> SEQUENCE: 117
catgtctacg gaggctgtaa cttttt                                          26

<210> SEQ ID NO 118
<211> LENGTH: 26
<212> TYPE: DNA
<213> ORGANISM: Nicotiana benthamiana

<400> SEQUENCE: 118
catgggtaga gccaaagagt gtgaac                                          26

<210> SEQ ID NO 119
<211> LENGTH: 26
<212> TYPE: DNA
<213> ORGANISM: Nicotiana benthamiana

<400> SEQUENCE: 119
catgttctgc tactcgacta tgagac                                          26

<210> SEQ ID NO 120
<211> LENGTH: 26
<212> TYPE: DNA
<213> ORGANISM: Nicotiana benthamiana

<400> SEQUENCE: 120
catgtgcttc aagacgtatc acttgt                                          26

<210> SEQ ID NO 121
<211> LENGTH: 26
<212> TYPE: DNA
<213> ORGANISM: Nicotiana benthamiana

<400> SEQUENCE: 121

```
catgtacact tcaagaatcc tactcc                                              26
```

<210> SEQ ID NO 122
<211> LENGTH: 26
<212> TYPE: DNA
<213> ORGANISM: Nicotiana benthamiana

<400> SEQUENCE: 122

```
catgggtaga tggatggttt gcttag                                              26
```

<210> SEQ ID NO 123
<211> LENGTH: 26
<212> TYPE: DNA
<213> ORGANISM: Nicotiana benthamiana

<400> SEQUENCE: 123

```
catggcacag ttaaaggatt ctctct                                              26
```

<210> SEQ ID NO 124
<211> LENGTH: 26
<212> TYPE: DNA
<213> ORGANISM: Nicotiana benthamiana

<400> SEQUENCE: 124

```
catggatgaa gaagctgctg ggtttt                                              26
```

<210> SEQ ID NO 125
<211> LENGTH: 26
<212> TYPE: DNA
<213> ORGANISM: Nicotiana benthamiana

<400> SEQUENCE: 125

```
catgacacgg tcaagcaaag atctgt                                              26
```

<210> SEQ ID NO 126
<211> LENGTH: 26
<212> TYPE: DNA
<213> ORGANISM: Nicotiana benthamiana

<400> SEQUENCE: 126

```
catgtgcagg actttagatc cttgca                                              26
```

<210> SEQ ID NO 127
<211> LENGTH: 26
<212> TYPE: DNA
<213> ORGANISM: Nicotiana benthamiana

<400> SEQUENCE: 127

```
catgttgtat aaagttgtaa cgaagc                                              26
```

<210> SEQ ID NO 128
<211> LENGTH: 26
<212> TYPE: DNA
<213> ORGANISM: Nicotiana benthamiana

<400> SEQUENCE: 128

```
catgatttta tggtaacttg attgat                                              26
```

<210> SEQ ID NO 129
<211> LENGTH: 26
<212> TYPE: DNA
<213> ORGANISM: Nicotiana benthamiana

<400> SEQUENCE: 129

-continued catgtttacc ctttgacggc ccaaat    26

<210> SEQ ID NO 130
<211> LENGTH: 26
<212> TYPE: DNA
<213> ORGANISM: Nicotiana benthamiana

<400> SEQUENCE: 130
catgcataac aatacattttt ggtcat    26

<210> SEQ ID NO 131
<211> LENGTH: 26
<212> TYPE: DNA
<213> ORGANISM: Nicotiana benthamiana

<400> SEQUENCE: 131
catgccttct tttctttgta ttatca    26

<210> SEQ ID NO 132
<211> LENGTH: 26
<212> TYPE: DNA
<213> ORGANISM: Nicotiana benthamiana

<400> SEQUENCE: 132
catggattaa catcattatt ctctgt    26

<210> SEQ ID NO 133
<211> LENGTH: 26
<212> TYPE: DNA
<213> ORGANISM: Nicotiana benthamiana

<400> SEQUENCE: 133
catgacactg ataactgccg aggatt    26

<210> SEQ ID NO 134
<211> LENGTH: 26
<212> TYPE: DNA
<213> ORGANISM: Nicotiana benthamiana

<400> SEQUENCE: 134
catgataacg tttatctaag aagagg    26

<210> SEQ ID NO 135
<211> LENGTH: 26
<212> TYPE: DNA
<213> ORGANISM: Nicotiana benthamiana

<400> SEQUENCE: 135
catggatgga aaacttagta ccaata    26

<210> SEQ ID NO 136
<211> LENGTH: 26
<212> TYPE: DNA
<213> ORGANISM: Nicotiana benthamiana

<400> SEQUENCE: 136
catgtgaaag aacagaccga gcttgt    26

<210> SEQ ID NO 137
<211> LENGTH: 26
<212> TYPE: DNA
<213> ORGANISM: Nicotiana benthamiana

<400> SEQUENCE: 137

```
catgaagtcc atcaaagtcc taggct                                          26

<210> SEQ ID NO 138
<211> LENGTH: 26
<212> TYPE: DNA
<213> ORGANISM: Nicotiana benthamiana

<400> SEQUENCE: 138
catgatcatt cttttgtata ccgtgt                                          26

<210> SEQ ID NO 139
<211> LENGTH: 26
<212> TYPE: DNA
<213> ORGANISM: Nicotiana benthamiana

<400> SEQUENCE: 139
catgtttgga gtaattctcc ttgtat                                          26

<210> SEQ ID NO 140
<211> LENGTH: 26
<212> TYPE: DNA
<213> ORGANISM: Nicotiana benthamiana

<400> SEQUENCE: 140
catggcatct cttgacaatg ttgggg                                          26

<210> SEQ ID NO 141
<211> LENGTH: 26
<212> TYPE: DNA
<213> ORGANISM: Nicotiana benthamiana

<400> SEQUENCE: 141
catggtcctt caaggggaag caggtg                                          26

<210> SEQ ID NO 142
<211> LENGTH: 26
<212> TYPE: DNA
<213> ORGANISM: Nicotiana benthamiana

<400> SEQUENCE: 142
catgtaagga gtgctactga aatgga                                          26

<210> SEQ ID NO 143
<211> LENGTH: 26
<212> TYPE: DNA
<213> ORGANISM: Nicotiana benthamiana

<400> SEQUENCE: 143
catgtggtct ctcaaatgtt ggaact                                          26

<210> SEQ ID NO 144
<211> LENGTH: 26
<212> TYPE: DNA
<213> ORGANISM: Nicotiana benthamiana

<400> SEQUENCE: 144
catgttgaac ctctgtaatt ccgatc                                          26

<210> SEQ ID NO 145
<211> LENGTH: 26
<212> TYPE: DNA
<213> ORGANISM: Nicotiana benthamiana

<400> SEQUENCE: 145
```
catgaacaca actagagtga agaagt                                    26

<210> SEQ ID NO 146
<211> LENGTH: 26
<212> TYPE: DNA
<213> ORGANISM: Nicotiana benthamiana

<400> SEQUENCE: 146
catgaagtta tacgccggac taaagt                                    26

<210> SEQ ID NO 147
<211> LENGTH: 26
<212> TYPE: DNA
<213> ORGANISM: Nicotiana benthamiana

<400> SEQUENCE: 147
catgaatgaa tttaacagtt caatat                                    26

<210> SEQ ID NO 148
<211> LENGTH: 26
<212> TYPE: DNA
<213> ORGANISM: Nicotiana benthamiana

<400> SEQUENCE: 148
catgatagga taacaaagat atatat                                    26

<210> SEQ ID NO 149
<211> LENGTH: 26
<212> TYPE: DNA
<213> ORGANISM: Nicotiana benthamiana

<400> SEQUENCE: 149
catgccttta gtactttgga tttggg                                    26

<210> SEQ ID NO 150
<211> LENGTH: 26
<212> TYPE: DNA
<213> ORGANISM: Nicotiana benthamiana

<400> SEQUENCE: 150
catggatcgg caaacaaaga gataat                                    26

<210> SEQ ID NO 151
<211> LENGTH: 26
<212> TYPE: DNA
<213> ORGANISM: Nicotiana benthamiana

<400> SEQUENCE: 151
catgttaaag tgaaacgcaa caatgg                                    26

<210> SEQ ID NO 152
<211> LENGTH: 26
<212> TYPE: DNA
<213> ORGANISM: Nicotiana benthamiana

<400> SEQUENCE: 152
catgttgatt atatgaccgg agggta                                    26

<210> SEQ ID NO 153
<211> LENGTH: 26
<212> TYPE: DNA
<213> ORGANISM: Nicotiana benthamiana

<400> SEQUENCE: 153

-continued catgacgaag ttccaacacg aagaga                                    26

<210> SEQ ID NO 154
<211> LENGTH: 26
<212> TYPE: DNA
<213> ORGANISM: Nicotiana benthamiana

<400> SEQUENCE: 154
catgataaat gggagaccct tgtact                                    26

<210> SEQ ID NO 155
<211> LENGTH: 26
<212> TYPE: DNA
<213> ORGANISM: Nicotiana benthamiana

<400> SEQUENCE: 155
catgatcatt ttcctgagat tcgacg                                    26

<210> SEQ ID NO 156
<211> LENGTH: 26
<212> TYPE: DNA
<213> ORGANISM: Nicotiana benthamiana

<400> SEQUENCE: 156
catgcaaaac ctaaaataac caaact                                    26

<210> SEQ ID NO 157
<211> LENGTH: 26
<212> TYPE: DNA
<213> ORGANISM: Nicotiana benthamiana

<400> SEQUENCE: 157
catggagttg tatcttgact gcttct                                    26

<210> SEQ ID NO 158
<211> LENGTH: 26
<212> TYPE: DNA
<213> ORGANISM: Nicotiana benthamiana

<400> SEQUENCE: 158
catgggatag cttttcatct ttggat                                    26

<210> SEQ ID NO 159
<211> LENGTH: 26
<212> TYPE: DNA
<213> ORGANISM: Nicotiana benthamiana

<400> SEQUENCE: 159
catgtaacca tacaagttga accatc                                    26

<210> SEQ ID NO 160
<211> LENGTH: 26
<212> TYPE: DNA
<213> ORGANISM: Nicotiana benthamiana

<400> SEQUENCE: 160
catgtgaatg acgcaaactt tcaagt                                    26

<210> SEQ ID NO 161
<211> LENGTH: 26
<212> TYPE: DNA
<213> ORGANISM: Nicotiana benthamiana

<400> SEQUENCE: 161 catgtttatag tatgagatag aggagt                                              26

<210> SEQ ID NO 162
<211> LENGTH: 26
<212> TYPE: DNA
<213> ORGANISM: Nicotiana benthamiana

<400> SEQUENCE: 162 catgtccct gtttgtatgt tctgtt                                                26

<210> SEQ ID NO 163
<211> LENGTH: 26
<212> TYPE: DNA
<213> ORGANISM: Nicotiana benthamiana

<400> SEQUENCE: 163
catggagcta caggacttca ttctcc                                               26

<210> SEQ ID NO 164
<211> LENGTH: 26
<212> TYPE: DNA
<213> ORGANISM: Nicotiana benthamiana

<400> SEQUENCE: 164
catgatctct ttcctgagat tcgtca                                               26

<210> SEQ ID NO 165
<211> LENGTH: 26
<212> TYPE: DNA
<213> ORGANISM: Nicotiana benthamiana

<400> SEQUENCE: 165
catgggcaga tcaatgggat ccagcc                                               26

<210> SEQ ID NO 166
<211> LENGTH: 26
<212> TYPE: DNA
<213> ORGANISM: Nicotiana benthamiana

<400> SEQUENCE: 166
catggaagaa gcaaccttag tgtggt                                               26

<210> SEQ ID NO 167
<211> LENGTH: 26
<212> TYPE: DNA
<213> ORGANISM: Nicotiana benthamiana

<400> SEQUENCE: 167
catgtggaat gttcgtattg tgaata                                               26

<210> SEQ ID NO 168
<211> LENGTH: 26
<212> TYPE: DNA
<213> ORGANISM: Nicotiana benthamiana

<400> SEQUENCE: 168
catgttgctg aagttttcac gggtgc                                               26

<210> SEQ ID NO 169
<211> LENGTH: 26
<212> TYPE: DNA
<213> ORGANISM: Nicotiana benthamiana

<400> SEQUENCE: 169
catgcaaggc cagtcggaga agaagg                                        26

<210> SEQ ID NO 170
<211> LENGTH: 26
<212> TYPE: DNA
<213> ORGANISM: Nicotiana benthamiana

<400> SEQUENCE: 170
catgagggat gagccaggag cacggc                                        26

<210> SEQ ID NO 171
<211> LENGTH: 26
<212> TYPE: DNA
<213> ORGANISM: Nicotiana benthamiana

<400> SEQUENCE: 171
catgttgcaa cttctagtca atgact                                        26

<210> SEQ ID NO 172
<211> LENGTH: 26
<212> TYPE: DNA
<213> ORGANISM: Nicotiana benthamiana

<400> SEQUENCE: 172
catgagcgga agctaacctg aatcca                                        26

<210> SEQ ID NO 173
<211> LENGTH: 26
<212> TYPE: DNA
<213> ORGANISM: Nicotiana benthamiana

<400> SEQUENCE: 173
catgcctgtg agcctgctgt tggtaa                                        26

<210> SEQ ID NO 174
<211> LENGTH: 26
<212> TYPE: DNA
<213> ORGANISM: Nicotiana benthamiana

<400> SEQUENCE: 174
catggcacca gcgtggaatg tcgcat                                        26

<210> SEQ ID NO 175
<211> LENGTH: 26
<212> TYPE: DNA
<213> ORGANISM: Nicotiana benthamiana

<400> SEQUENCE: 175
catggggata tagcaagatc gtgaat                                        26

<210> SEQ ID NO 176
<211> LENGTH: 26
<212> TYPE: DNA
<213> ORGANISM: Nicotiana benthamiana

<400> SEQUENCE: 176
catgttatct ttccaataga ggcgag                                        26

<210> SEQ ID NO 177
<211> LENGTH: 26
<212> TYPE: DNA
<213> ORGANISM: Nicotiana benthamiana

<400> SEQUENCE: 177
catgagactc taaacaattt cgcttg                                    26

<210> SEQ ID NO 178
<211> LENGTH: 26
<212> TYPE: DNA
<213> ORGANISM: Nicotiana benthamiana

<400> SEQUENCE: 178
catgcagcaa agaccaagaa cagccc                                    26

<210> SEQ ID NO 179
<211> LENGTH: 26
<212> TYPE: DNA
<213> ORGANISM: Nicotiana benthamiana

<400> SEQUENCE: 179
catgccgaag caaatccacg aaatca                                    26

<210> SEQ ID NO 180
<211> LENGTH: 26
<212> TYPE: DNA
<213> ORGANISM: Nicotiana benthamiana

<400> SEQUENCE: 180
catgcttaca aagggaatcc agctac                                    26

<210> SEQ ID NO 181
<211> LENGTH: 26
<212> TYPE: DNA
<213> ORGANISM: Nicotiana benthamiana

<400> SEQUENCE: 181
catggggtct cccgctggta aggtat                                    26

<210> SEQ ID NO 182
<211> LENGTH: 26
<212> TYPE: DNA
<213> ORGANISM: Nicotiana benthamiana

<400> SEQUENCE: 182
catgacgcgc ttaacctaca ctcttg                                    26

<210> SEQ ID NO 183
<211> LENGTH: 26
<212> TYPE: DNA
<213> ORGANISM: Nicotiana benthamiana

<400> SEQUENCE: 183
catgaggagg ctagaaggaa gaatgt                                    26

<210> SEQ ID NO 184
<211> LENGTH: 26
<212> TYPE: DNA
<213> ORGANISM: Nicotiana benthamiana

<400> SEQUENCE: 184
catgagggat gaaccaggag ccagac                                    26

<210> SEQ ID NO 185
<211> LENGTH: 26
<212> TYPE: DNA
<213> ORGANISM: Nicotiana benthamiana

<400> SEQUENCE: 185

```
catgatttgt aactattggg gattct                                          26

<210> SEQ ID NO 186
<211> LENGTH: 26
<212> TYPE: DNA
<213> ORGANISM: Nicotiana benthamiana

<400> SEQUENCE: 186
catggatata tggcaattgc gtttgt                                          26

<210> SEQ ID NO 187
<211> LENGTH: 26
<212> TYPE: DNA
<213> ORGANISM: Nicotiana benthamiana

<400> SEQUENCE: 187
catgggtgct gagatggttt aatggt                                          26

<210> SEQ ID NO 188
<211> LENGTH: 26
<212> TYPE: DNA
<213> ORGANISM: Nicotiana benthamiana

<400> SEQUENCE: 188
catgtaattt ggcggggagt aatgta                                          26

<210> SEQ ID NO 189
<211> LENGTH: 26
<212> TYPE: DNA
<213> ORGANISM: Nicotiana benthamiana

<400> SEQUENCE: 189
catgaataaa tgctactcta atagct                                          26

<210> SEQ ID NO 190
<211> LENGTH: 26
<212> TYPE: DNA
<213> ORGANISM: Nicotiana benthamiana

<400> SEQUENCE: 190
catgacggaa aagccaatta tcaagt                                          26

<210> SEQ ID NO 191
<211> LENGTH: 26
<212> TYPE: DNA
<213> ORGANISM: Nicotiana benthamiana

<400> SEQUENCE: 191
catgattggg caatttggtg ttggtt                                          26

<210> SEQ ID NO 192
<211> LENGTH: 26
<212> TYPE: DNA
<213> ORGANISM: Nicotiana benthamiana

<400> SEQUENCE: 192
catgattttc aaggacggag agaaga                                          26

<210> SEQ ID NO 193
<211> LENGTH: 26
<212> TYPE: DNA
<213> ORGANISM: Nicotiana benthamiana

<400> SEQUENCE: 193
```

```
catgccaccg gggtccacaa cgtgct                                           26
```

<210> SEQ ID NO 194
<211> LENGTH: 26
<212> TYPE: DNA
<213> ORGANISM: Nicotiana benthamiana

<400> SEQUENCE: 194

```
catgctgccc aactttgtgt attggc                                           26
```

<210> SEQ ID NO 195
<211> LENGTH: 26
<212> TYPE: DNA
<213> ORGANISM: Nicotiana benthamiana

<400> SEQUENCE: 195

```
catgggtttc agcttgtttg attaag                                           26
```

<210> SEQ ID NO 196
<211> LENGTH: 26
<212> TYPE: DNA
<213> ORGANISM: Nicotiana benthamiana

<400> SEQUENCE: 196

```
catgtataaa ttgtgtaatg ttgtgt                                           26
```

<210> SEQ ID NO 197
<211> LENGTH: 46
<212> TYPE: DNA
<213> ORGANISM: Artificial Sequence
<220> FEATURE:
<223> OTHER INFORMATION: Description of Artificial Sequence: Synthetic
      Linker A

<400> SEQUENCE: 197

```
tttggatttg ctggtgcagt acaactaggc ttaatacagc agcatg              46
```

<210> SEQ ID NO 198
<211> LENGTH: 42
<212> TYPE: DNA
<213> ORGANISM: Artificial Sequence
<220> FEATURE:
<223> OTHER INFORMATION: Description of Artificial Sequence: Synthetic
      Linker A

<400> SEQUENCE: 198

```
ctgctgtatt aagcctagtt gtactgcacc agcaaatcca aa                  42
```

<210> SEQ ID NO 199
<211> LENGTH: 44
<212> TYPE: DNA
<213> ORGANISM: Artificial Sequence
<220> FEATURE:
<223> OTHER INFORMATION: Description of Artificial Sequence: Synthetic
      Linker B

<400> SEQUENCE: 199

```
tttctgctcg aattcaagct tctaacgatg tacgcagcag catg                 44
```

<210> SEQ ID NO 200
<211> LENGTH: 40
<212> TYPE: DNA
<213> ORGANISM: Artificial Sequence
<220> FEATURE:
<223> OTHER INFORMATION: Description of Artificial Sequence: Synthetic
      Linker B

<400> SEQUENCE: 200
ctgctgcgta catcgttaga agcttgaatt cgagcagaaa                                40

<210> SEQ ID NO 201
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(40)
<223> OTHER INFORMATION: n is a, c, g, t, or any arbitrary nucleotide
      and up to 10 of them may be present or absent

<400> SEQUENCE: 201
nnnnnnnnnn nnnnnnnnnn nnnnnnnnnn nnnnnnnnnn cagcagcatg                    50

<210> SEQ ID NO 202
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
aaaaaaaaaa aaaaa                                                           15

<210> SEQ ID NO 203
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tttttttttt ttttttttg acgac                                                 25

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
aaaaaaaaaa aaaaagtcgt c                                                    21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tttttttttt ttttgacga c                                                     21

<210> SEQ ID NO 206
<211> LENGTH: 12
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 206
aaaaaactgc tg                                                              12

<210> SEQ ID NO 207
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207 tttttttgacg ac                                                             12

<210> SEQ ID NO 208
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
cagcagcatg aaaaaactgc tg                                                   22

<210> SEQ ID NO 209
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gtactttttt gacgac                                                          16

<210> SEQ ID NO 210
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210 tttttttgacg ac                                                             12

<210> SEQ ID NO 211
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
cagcagcatg                                                                 10
```